(12) United States Patent
Moe

(10) Patent No.: US 8,298,577 B2
(45) Date of Patent: *Oct. 30, 2012

(54) EFFERVESCENT ORAL OPIATE DOSAGE FORMS AND METHODS OF ADMINISTERING OPIATES

(75) Inventor: Derek Moe, Mound, MN (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/955,439

(22) Filed: Nov. 29, 2010

(65) Prior Publication Data

US 2011/0071181 A1 Mar. 24, 2011

Related U.S. Application Data

(63) Continuation of application No. 11/026,759, filed on Dec. 30, 2004, now Pat. No. 7,862,833.

(60) Provisional application No. 60/533,619, filed on Dec. 31, 2003, provisional application No. 60/615,665, filed on Oct. 4, 2004, provisional application No. 60/615,785, filed on Oct. 4, 2004.

(51) Int. Cl.
*A61K 9/20* (2006.01)
*A61K 9/46* (2006.01)

(52) U.S. Cl. ......... 424/464; 424/465; 424/466; 424/434

(58) Field of Classification Search ................ None
See application file for complete search history.

(56) References Cited

U.S. PATENT DOCUMENTS

| | | | |
|---|---|---|---|
| 1,262,888 A | 4/1918 | Westlake | |
| 2,887,437 A | 5/1959 | Klioze et al. | |
| 3,042,531 A | 7/1962 | Leal et al. | |
| 3,131,123 A | 4/1964 | Masquelier | |
| 3,577,490 A | 5/1971 | Welsh et al. | |
| 3,888,976 A | 6/1975 | Mlkvy et al. | |
| 3,961,041 A | 6/1976 | Nishimura et al. | |
| 3,962,417 A | 6/1976 | Howell | |
| 3,972,995 A | 8/1976 | Tsuk et al. | |
| 4,126,684 A * | 11/1978 | Robson et al. | 514/271 |
| 4,147,768 A | 4/1979 | Shaffer et al. | |
| 4,187,286 A | 2/1980 | Marcus | |
| 4,289,751 A | 9/1981 | Windheuser | |
| 4,370,160 A | 1/1983 | Ziemelis | |
| 4,443,428 A | 4/1984 | Oshlack et al. | |
| 4,493,848 A | 1/1985 | LaHann et al. | |
| 4,503,031 A | 3/1985 | Glassman | |
| 4,599,342 A | 7/1986 | LaHann | |
| 4,613,497 A | 9/1986 | Chavkin | |
| 4,639,368 A | 1/1987 | Niazi et al. | |
| 4,671,953 A | 6/1987 | Stanley et al. | |
| 4,687,662 A | 8/1987 | Schobel | |
| 4,689,218 A | 8/1987 | Gazzaniga et al. | |
| 4,717,723 A | 1/1988 | Sugden | |
| 4,725,427 A | 2/1988 | Ashmead et al. | |
| 4,753,792 A | 6/1988 | Aberg | |
| 4,756,710 A | 7/1988 | Bondi et al. | |
| 4,853,211 A | 8/1989 | Kurobe et al. | |
| 4,863,737 A | 9/1989 | Stanley et al. | |
| 4,876,039 A | 10/1989 | Lo et al. | |
| 4,940,588 A | 7/1990 | Sparks et al. | |
| 4,952,402 A * | 8/1990 | Sparks et al. | 424/419 |
| 5,002,771 A | 3/1991 | Purkaystha et al. | |
| 5,004,601 A | 4/1991 | Snipes | |
| 5,028,411 A | 7/1991 | Callingham et al. | |
| 5,053,396 A | 10/1991 | Blass | |
| 5,055,306 A | 10/1991 | Barry et al. | |
| 5,073,374 A | 12/1991 | McCarty | |
| 5,102,665 A | 4/1992 | Schaeffer | |
| 5,102,666 A | 4/1992 | Acharya | |
| 5,135,752 A | 8/1992 | Snipes | |
| 5,178,878 A | 1/1993 | Wehling et al. | |
| 5,223,264 A | 6/1993 | Wehling et al. | |
| 5,234,957 A | 8/1993 | Mantelle | |
| 5,288,497 A | 2/1994 | Stanley et al. | |
| 5,314,904 A | 5/1994 | Egidio et al. | |
| 5,387,420 A | 2/1995 | Mitchell | |
| 5,445,827 A | 8/1995 | Fritsch et al. | |
| 5,458,879 A | 10/1995 | Singh et al. | |
| 5,464,632 A | 11/1995 | Cousin et al. | |
| 5,468,504 A | 11/1995 | Schaeffer | |
| 5,503,846 A | 4/1996 | Wehling et al. | |
| 5,550,861 A | 8/1996 | Makino | |
| 5,559,096 A | 9/1996 | Edwards et al. | |
| 5,607,697 A | 3/1997 | Alkire et al. | |
| 5,624,687 A | 4/1997 | Yano et al. | |
| 5,626,866 A | 5/1997 | Ebert et al. | |
| 5,635,210 A | 6/1997 | Allen, Jr. et al. | |

(Continued)

FOREIGN PATENT DOCUMENTS

CA 2254060 5/1997

(Continued)

OTHER PUBLICATIONS

20080603_D01_Complaint, 2008.
20080722_CEPHetal_v_Barretal_Complaint_Patent_Infringement, 2008.
20080127_Cephetal_v_Barretal_Answer_Affirmative_Defenses_and_Counterclaims, 2008.
Sterne_Kessler_June_9_2008.
Sterne_Kessler_June_27_2008.
20100809_D256_Redacted_Defs_Responsive_PostTrial_Brief, 2010.
20100811_D257_Redacted_Watson_Motion_toStrike, 2010.
20100811_D258_Redated_Declof_Braunel_re_Motto_Strike_Exp_Testimony, 2010.
20100813_D260_Redacted_Watson_MottoExcludeCO2Testing, 2010.
20100820_D263_RedactedBookerDecIISOReplyPostTrialBriefwithEx1_and2, 2010.
20100820_D264_Redacted_PltfsOpptoMotiontoStrike, 2010.

(Continued)

*Primary Examiner* — Robert A Wax
*Assistant Examiner* — Olga V Tcherkasskaya
(74) *Attorney, Agent, or Firm* — Cephalon, Inc.

(57) ABSTRACT

Opiate containing dosage forms and methods using same are described. These dosage forms include substantially less opiates by weight than known oral formulations. These dosage forms are intended for oral administration across the oral mucosa.

10 Claims, No Drawings

U.S. PATENT DOCUMENTS

| | | | |
|---|---|---|---|
| 5,646,151 | A | 7/1997 | Kruse et al. |
| 5,656,284 | A | 8/1997 | Balkin |
| 5,720,974 | A | 2/1998 | Makino et al. |
| 5,785,989 | A | 7/1998 | Stanley et al. |
| 5,807,688 | A | 9/1998 | Blackburn et al. |
| 5,851,553 | A | 12/1998 | Myers et al. |
| 5,853,748 | A | 12/1998 | New |
| 5,900,252 | A | 5/1999 | Calanchi et al. |
| 5,914,129 | A * | 6/1999 | Mauskop ............... 424/464 |
| 5,952,004 | A | 9/1999 | Rudnic et al. |
| 5,958,455 | A | 9/1999 | Roser et al. |
| 5,958,458 | A | 9/1999 | Norling et al. |
| 6,034,085 | A | 3/2000 | Joshi et al. |
| 6,068,853 | A | 5/2000 | Giannos et al. |
| 6,071,539 | A | 6/2000 | Robinson et al. |
| 6,106,861 | A | 8/2000 | Cheveau |
| 6,117,912 | A | 9/2000 | DiSanto |
| 6,129,906 | A | 10/2000 | Steventon |
| 6,155,423 | A | 12/2000 | Katzner et al. |
| 6,171,617 | B1 | 1/2001 | Gruber |
| 6,190,697 | B1 | 2/2001 | Gergely et al. |
| 6,200,604 | B1 | 3/2001 | Pather et al. |
| 6,242,002 | B1 | 6/2001 | Tritthart et al. |
| 6,264,981 | B1 | 7/2001 | Zhang et al. |
| 6,316,027 | B1 | 11/2001 | Johnson et al. |
| 6,326,360 | B1 | 12/2001 | Kanazawa et al. |
| 6,326,384 | B1 | 12/2001 | Whittle et al. |
| 6,350,470 | B1 | 2/2002 | Pather et al. |
| 6,368,625 | B1 | 4/2002 | Siebert et al. |
| 6,391,335 | B1 | 5/2002 | Pather et al. |
| 6,488,961 | B1 | 12/2002 | Robinson et al. |
| 6,509,036 | B2 | 1/2003 | Pather et al. |
| 6,576,250 | B1 | 6/2003 | Pather et al. |
| 6,641,838 | B2 | 11/2003 | Pather et al. |
| 6,680,071 | B1 | 1/2004 | Johnson et al. |
| 6,759,059 | B1 | 7/2004 | Petterson et al. |
| 6,761,910 | B1 | 7/2004 | Petterson et al. |
| 6,764,696 | B2 | 7/2004 | Pather et al. |
| 6,974,590 | B2 | 12/2005 | Pather et al. |
| 7,670,617 | B2 | 3/2010 | Pather et al. |
| 7,858,121 | B2 * | 12/2010 | Moe et al. .............. 424/464 |
| 7,862,832 | B2 * | 1/2011 | Moe et al. .............. 424/464 |
| 7,862,833 | B2 * | 1/2011 | Moe ...................... 424/464 |
| 2001/0006677 | A1 | 7/2001 | McGinity et al. |
| 2001/0041165 | A1 | 11/2001 | Katdare et al. |
| 2002/0110578 | A1 * | 8/2002 | Pather et al. ........... 424/434 |
| 2002/0160991 | A1 | 10/2002 | Shao |
| 2003/0035839 | A1 * | 2/2003 | Hirsh et al. ............ 424/471 |
| 2003/0088236 | A1 * | 5/2003 | Johnson et al. ......... 604/890.1 |
| 2004/0213855 | A1 | 10/2004 | Petterson et al. |
| 2005/0037072 | A1 | 2/2005 | Pather et al. |
| 2005/0042281 | A1 | 2/2005 | Singh et al. |
| 2005/0142197 | A1 | 6/2005 | Moe et al. |
| 2005/0142198 | A1 | 6/2005 | Moe et al. |
| 2005/0163838 | A1 | 7/2005 | Moe |
| 2005/0169989 | A1 | 8/2005 | Moe et al. |
| 2006/0292219 | A1 | 12/2006 | Pather et al. |
| 2007/0036853 | A1 | 2/2007 | Agarwal et al. |
| 2008/0226717 | A1 * | 9/2008 | Oury et al. ............. 424/474 |
| 2009/0263476 | A1 * | 10/2009 | Jobdevairakkam et al. .. 424/452 |

FOREIGN PATENT DOCUMENTS

| | | | |
|---|---|---|---|
| CA | 2326502 | A1 | 10/1999 |
| CA | 2218370 | | 10/2006 |
| DE | 4139883A12 | | 6/1993 |
| EP | 0197504 | A2 | 10/1986 |
| EP | 0275834 | A1 | 7/1988 |
| EP | 0354973 | A1 | 2/1990 |
| EP | 0361680 | A2 | 4/1990 |
| EP | 0396335 | | 11/1990 |
| EP | 1062952 | | 12/2000 |
| EP | 1067905 | A1 | 1/2001 |
| FR | 2732217 | A1 | 10/1996 |
| GB | 3160 | | 0/1878 |
| GB | 1212704 | A | 11/1970 |
| GB | 2307857 | | 6/1997 |
| JP | 7277959 | | 10/1995 |
| NL | 7302521 | A | 2/1973 |
| TW | 36236 | | 4/1981 |
| TW | 40484 | | 12/1981 |
| TW | 200611697 | | 4/2006 |
| WO | WO9104757 | | 4/1991 |
| WO | WO9302662 | A1 | 2/1993 |
| WO | WO9507701 | | 3/1995 |
| WO | WO9527482 | A1 | 10/1995 |
| WO | WO9534291 | A1 | 12/1995 |
| WO | WO96029993 | | 10/1996 |
| WO | WO9706786 | A1 | 2/1997 |
| WO | WO9717067 | | 5/1997 |
| WO | WO9945934 | A1 | 9/1999 |
| WO | WO9949842 | A1 | 10/1999 |
| WO | WO0009093 | | 2/2000 |
| WO | WO0059423 | A1 | 10/2000 |
| WO | WO0180822 | A2 | 11/2001 |
| WO | WO2005065318 | | 7/2005 |
| WO | WO2005065319 | A2 | 7/2005 |

OTHER PUBLICATIONS

20100820_D262_Redacted_Pltfs_Reply_PostTrial_Brief_corrected, 2010.
20100820_D261_Redacted_PostTrial_Brief_ofWatson, 2010.
20100930_D288_Redacted_D279CorrectedWatson_Reply_Post_Trial_Brief, 2010.
20110120_D301_Redacted_PlaintiffsBrief_iso_Motion_to_StrikeDefsNotofSubsequentAuthority, 2011.
20110120_D302_Redacted_BookerDeclisoPlaintiffsMotionto_Strike, 2011.
20110125_D303_Redacted_D295_DefsAnsweringBriefinOpptoMottoStrike, 2011.
20110125_D304_Redacted_D295Gwin_DeclisoDefAns_BriefreMottoStrike, 2011.
20110125_D305_Redacted_D296_Suzuki_Decliso_Def_Ans_Brief_re_MottoStrike, 2011.
20100820_D265_Redacted_BookerDeclISOOpptoMotiontoStrike_withEx_AB, 2010.
20110203_D310_Redacted_D298_DefsMottoVacate_10_28_10_Order, 2011.
20110203_D311_Redacted_D299_Boyer_DeclisoMotiontoVacate_w_Exh_1, 2011.
20110203_D312_Redacted_D300_Suzuki_Decl_isoMotiontoVacate_w_Exhs1_3, 2011.
20110204_D316_Redacted_D306_Pltfs_Reply_Motiontostrik1, 2011.
20110204_D319_Redacted_D307_Pltfs_OpptoDefsMotiontoVacate, 2011.
20110204_D320_Redacted_D308_CampbellDeclisoPltfsOpptoDefsMotion_toVacate, 2011.
20110204_D321_Redacted_D309_bradwayDeclisoPltfsOpp_toDefsMotion_toVacate, 2011.
20110211_324_Redacted_D315BoyerDeclisoReplyreMotiontoVacate, 2011.
20110311_D327_Opinion_1, 2011.
20080415_Watson_NotificationofCertification, 2008.
20110211_D323_Redacted_D313_Watson_Reply_re_MotiontoVacate, 2011.
20080812_Cephalon_v_Barr_Answer_Affirmative_Defenses, 2008.
20110224_D01_Civil_Cover_Sheet, 2011.
20110224_D01_Complaint_w_Exhibits_1, 2011.
2011_02_24_D02_NoticeofAvailabilityof_Magistrate, 2011.
20110224_D03_CephalonDisclosureStatement, 2011.
20110224_D04_CIMADisclosureStatement, 2011.
20110224_D05_SupplInfoforAndAPatentCases, 2011.
20110225_D06_Report_of_FilingtoUSPTO, 2011.
20110309_D07_ExecutedSummonsreMylan_Pharm_Served_22511, 2011.
20110309_D08_ExecutedSummonsreMylanInc_Served_22511, 2011.
20110318D09_Stipto, 2011.
20110322DXXOrderGranting_StiptpExtendTime, 2011.
20110325_D10_Substitution_of_Counsel, 2011.

20110325_D11_Mylan_Def_AnswertoComplaintCounterclaim_1, 2011.
20110325_D12_Mylan_PharmaceuticalDisclosureStatement_1, 2011.
20110325_D13MylanInc_DisclosureStatement_1, 2011.
20110329_D14_MylanProHacMotreFiggandBhattofRothwellFigg_1, 2011.
20110411_D15_Order_Setting_Scheduling_Teleconference_42911, 2011.
20090216_D01_Civil_Cover_CephalonvSandoz, 2009.
20090216_D01_Complaint_CephalonvSandoz, 2009.
20100216_D01_Complaint_Exh_A_604Patent, 2010.
20100216_D01_Complaint_ExhB_590_Patent1, 2010.
20100216_D02_Notice_Consent_Reference_to_a_Magistrate, 2010.
20081103_D11_Pltf_AnswertoCounterclaims, 2008.
20090112_Watson_Response_to_1_Set_of_Interrogatories_Nos1_11, 2009.
20081223_Barrs_First_Set_of_Interrogatories_No1_10, 2008.
20081222_Cephetal_v_Barretal_Stern_Kessler_ltr, 2008.
20110318_Coster_ltr_re_Protecting_Funding_for_FDA_w_Exhibits_1, 2011.
20100311_DXX_Orderre_Stip_to_Extend_TimetoAnswer, 2010.
20100322_D08_Sandoz_Answer_w_Counterclaims, 2010.
20100322_D09_Sandoz_Corporate_Disclosure_Statement, 2010.
20100322_D10_Sandoz_ProHacMot_reGargano_ofMcDermott_Will, 2010.
20100322_D11_Sandoz_Pro_Hac_MotreGarcha_Dolkas_Chang_BoyleofMcDermott_Will, 2010.
20100331_DXX_Text_Order_re_ProHac_Adm_ofMcDermott_AttysforSandoz, 2010.
20100415_D12_AnswertoCounterclaims, 2010.
20100420_D13_OrderSettingSchedulingTelecon, 2010.
20100511_D14_ProposedSchedulingOrder, 2010.
20100511_D15_Order_re_Telecon_Court_Docket_Error, 2010.
20100520_D16_Final_Proposed_Scheduling_Order, 2010.
20100524_D17_Order_re_Telecon_Court_Docket_Error, 2010.
20100525_D18_NOSre_Plaintiffs_Initial_Disclosures, 2010.
20100525_D19_NOSre_Defendants_Initial_Disclosures, 2010.
20100603_D20_Order_RegardingDiscoveryMatters, 2010.
20100603_DXX_SchedulingOrderEntered, 2010.
20100720_D21_OrderSchedulingADR_Telecon_8410, 2010.
20100729_D22_Stipulated_Amendmentto_Scheduling_OrderreDocProduction_1, 2010.
20100805_D23_Order_Regarding_Discovery_Matters_MPT1, 2010.
20100805_D24_Order_Scheduling_ADR_Telecon_81810_1, 2010.
20100813_D25_Order_ReschedulingADR_Telecon_82310_1, 2010.
20100830_D26_Cephalon_NOS_re_1st_Set_Rogs_and_RFPs_to_Sandoz, 2010.
20100830_D27_2nd_Stipulated_Amendment_to_Scheduling_Order_re_Doc_Production_1, 2010.
20100831_D28_Order_Scheduling_ADR_Telecon_92210_1, 2010.
20100831_D29_Sandoz_NOS_re_1st_Set_RogsandRFPSto_Cephalon_1, 2010.
20100901_D30_Cephalon_NOAof_Compton_1, 2010.
20100922_D31_Order_setting_Teleconference_with_MJ_Thynge_1, 2010.
20101001_D32_Stipulated_Amendment_1, 2010.
20101005_DXX_Text_Order, 2010.
20101012_D33_Cephalon_NOS_RespandObjto_Sandoz_1, 2010.
20101012_D34_Sandoz_NOS_1, 2010.
20101018_D35_SandozNOS_re_Inventor_1, 2010.
20101018_D36_Cephalon_30b6_NOD_to_Sandoz, 2010.
20101025_D37_Order_Setting_Mediation_Conference_1, 2010.
20101025_D38_Cephalon_NOD_of_AlisonSherwood, 2010.
20101025_D39_Cephalon_NODof_Ellen_Camos, 2010.
20101025_D40_CephalonNODof_IndraniNandi, 2010.
20101026_D41_Sandoz_Notof_Subpoenasto_LernerDavid, 2010.
20101026_D42_CephalonNotofSubpoenato_Navinta_LLC, 2010.
20101027_D43_Sandoz_NotofSubpoenato_Univ_of_WisconsinMadison, 2010.
20101028_D44_Sandoz_NOS_re_2ndNotice_of30b6_toCIMAandCephalon, 2010.
20101028_D45_SandozNot_ofSubpoena_toJasonGarbell, 2010.
20101101_D46_CephalonSubpoenaExecuted102610reNavinta, 2010.
20101101_D47_Cephalon_1, 2010.
20101105_D48_Plaintiffs_NOSreObjsto_LernerDavidSubpoenas, 2010.
20101112_D49_Cephalon_NOSreSupplRespto1stSetofRogs_Nos3and5_1, 2010.
20101118_D50_Sandoz_NOSObjstoCephalonSubpoenatoNavinta, 2010.
20101118_D51_SandozNotofSubpoenas_toAnestaColemanZhang, 2010.
20101124_D52_NOS, 2010.
20101124_D53_NOS_re_RespsandObjs-SandozSubpoenatoDennisColeman, 2010.
20101201_D54_Sandoz_NOSreObjsandRespsto30b6NOD, 2010.
20101206_D55_CephalonandCIMA_NOSreRespsandObjstoSandoz2nd30b6NOD, 2010.
20101210_D56_OrderSettingContinuedMediationConference_1, 2010.
20101229_D57_Cephalon_AmendedNODofAlisonSherwood, 2010.
20110106_D58_ProposedStipulatedProtectiveOrder, 2011.
20110107_DXX_Signed_Protective_Order, 2011.
20110114_D59_Fourth_Stipulated_Amendment_to_Scheduling_Order, 2011.
20110119_D60_Cephalon_NOS_reSuppLRespsObjs_to_Sandoz_30b6_NODs, 2011.
20110119_DXX_TextOrderGranting_4th_Stip_Amendment_toSched_Order, 2011.
20110201_D61_Order_Setting_TelecontoDiscuss_2711_Mediation_13111_1, 2011.
20110201_DXX_Email_to_JudgeThynge_frMarsdenre_parties_availability_for_mediation_1, 2011.
20110202_D62_Order_Setting_Telecon_re_DatesforMediation_2711_1, 2011.
20110202_D63_OrderSettingTeleconre_Navinta_DiscoveryIssue_21111_1, 2011.
20110208_D64_CephalonNOD_ofSunilVandse, 2011.
20110208_D65_Cephalon_NODOfMatthewBohlman, 2011.
20110211_D68_Cephalon_NOSre3rd_Suppl_RespandObj_to_Sandoz1stRogs, 2011.
20110214_D69_Order_Setting_Mediation_Conference_32311_1, 2011.
20110214_D70_Sandoz_NOSre3rdSuppl, 2011.
20110216_D73_Redacted_D66_Ltr_toMagJ_Thynefr_Marsdenrediscovery_disputeExhA-K, 2011.
20110216_D73_Redacted_D66_LtrtoMagJThyne_fr_Marsden_rediscoverydispute, 2011.
20110216_D74CephalonNODOfJessicaMartori, 2011.
20110217_D75_RedactedD67Ltrto_MagJThyngefr_Shawrediscoverydispute, 2011.
20110217_D76_Redacted_D72_LtrtoMagJThynge_fr_Shawre_Cephalonmotto_compel_Navinta, 2011.
20110225_D77_Plaintiff_NOS_re_Opening_Expert_Reports_1, 2011.
20110228_D78_Defendant_NOS_re_Expert_Report, 2011.
20110308_D80_Order_Setting_TeleconreDiscoveryIssue_1, 2011.

20110310_D81_Redacted_D79_LtrtoMagJThynge_frMarsdenrependingmotion_tocompeldiscovery, 2011.
20110310_D81_Redacted_D79Ltr_to_MagJThynge_fr_Marsden_Att_1_6_1, 2011.
20110311_D83_OrderTelecom_1, 2011.
20110317_D84_Redacted_D82_Sealed_LtrtoMagJThyngefrShawre_Pltf_3311letterw_ExhA_D_1, 2011.
20110325_D85_Order_Setting_Discovery_Teleconference_w_JudgeThynge_1, 2011.
20110325_D86_Plaintiffs_NOSofWilliams_Rebuttal_Expert_Report_1, 2011.
20110328_D88_Plaintiffs_Motionto_Stay_1, 2011.
20110328_D88_Plaintiffs_Motionto_Stay_ProposedOrder_1, 2011.
20110329_D90_Sandoz_1, 2011.
20110329_D91_LtrtoMagJThyngefr_McCannenclcourtes_copyofMottoStay_1, 2011.
20110404_D94_Redacted_D87_LtrtoMagJThynge_fr_McCann_rediscoveryextension_ProposedOrder_1, 2011.
20110404_D94_Redacted_D87LtrtoMagJThyngefrMcCannre_discoveryextension_1, 2011.
20110404_D95_Redacted_D89_Opening_Brief_Ex_AB_1, 2011.
20110405_D95_Redacted_D89_OpeningBriefisoMotion_toStay_1, 2011.
20110405_D96_Redacted_D92Corrected_Ltr_toMagJThyngefrPoffrePltfs328_discovery_ltr_1, 2011.
20110411_D97_Fifth_Stipulated_Amended_to_Scheduling_Order, 2011.
20100427_Annex_to_Communication_re_04815716_8, 2010.
Search_Report_PCTUS0443703_20051101_2pgs, 2005.
EP_Supplementary_Partial_Search_Report_EP04815715_dated_11142007, 2007.
20090116_Cephetal_v_Watsonetal_Amended_Complaint_for_Patent_Infringement, 2009.
20090223_Cephetal_v_Barretal_Answer_Affirmative_Defenses_and_Counterclaims, 2009.
20090427_Answer_to_Counterclaims_to_amended_Complaint_CephalonvWatson, 2009.
20100513_D240_Redacted_D205_Watson_Ans_Briefin_Opp_to_Mot_toAmend_PO, 2010.
20090109_Barrs_respns_to_pltff_first_set_of Interrogs, 2009.
20090112_Watson_Response_to_1_Set_of Interrogatories_Nos1_11, 2009.
20090211_Barr_Responses_and_Objections_to_Cephetal_Second_setof_Interrogs, 2009.
20090217_Cephetal_v_Barretal_Answera_to_Counterclaims, 2009.
20090313_Cepheal_Barretal_Answer_to_Counterclaims, 2009.
20090330 Cephetal_v_Watsonetal_Dfndnts_Spplmntl_Obj_and Rspns_to_Plntfs_Frst_Set_of_Interrogs, 2009.
20090429_Cephetal_v_Watsonetal_Plaintiffs_Response_to_Defendants_Invalidity_Contentions, 2009.
20090429_Defendants_Send_Spplemntl_Objs_and_Rspns_to_Plntffs_frst_setof_Interrogs, 2009.
20090518_D144_Cephalon_AnswertoCounterclaims, 2009.
20090529_Fish_Richardson_Cephetal_v_Watson_Stronski_ltr, 2009.
20090330 Cephetal_v_Barretal_Plaintiffs_Supplemental_Responseto_Defendants_first_set_ofInterrogs, 2009.
20090529_Cephetal_v_Barr_Plnts_Send_Sup_Rspnse_to_Dfndnts_frst_set_of_Interoggs, 2009.
20090126_Cephetal_v_Barretal_Plntfs_Rspns_to_Dfndnts_frst_set_of_Interoggs, 2009.
20110329_Fish_Richardson_Letter, 2011.

20090130_Cephalon_CIMA_Complaint_for_Patent_Infringement, 2009.
20081029_Cephalon_Cima_Complaint_for_Patent_Infringement, 2008.
20090130_Cephetal_v_Barr_Complaint_for_Patent_Infringement, 2009.
20090127_Cephetal_v_Barretal_Answer_Affirmative_Defenses_and_Counterclaims, 2009.
20110928_ParaIV_Mylan_Fentora, 2011.
Eichman_Increased_Drug_Absorption_Through_Caronation_Thesis_1995.
20100730 D252 Booker Deciso Responsive PostTrial Brief on Validity Exh 1-5, 2010.
20100216 D03 Cephalon Corporate Disclosure Statement, 2010.
20100216 D04 CIMA Corporate Disclosure Statement, 2010.
Supplementary_European_Search_Report_EP00926341_2005, 2005.
20000914_US_Patent_Application_09661693, 2009.
20080602_D05ReportonFilingofanAction, 2008.
20080715_D12_Watson_Pharmaceuticals_Motion, 2008.
20080715_D15_WatsonLabs_MTD, 2008.
20080722_D18_Redacted_D17WatsonLabsOpeningBriefisoMTD, 2008.
20080722_D19_Redacted_D14, 2008.
20090306_D96_Watson_Opening_Brief_MTD_Amended_Complaint, 2009.
20090306_D110_Redacted_D97_DeclofParkisoWatsonsoMTDreAmendedComplaint_Exh1_30, 2009.
20090306_D111_Redacted_D99_Watson_LabsReplyBriefisoMTD, 2009.
20090323_D119_Redacted_D117, 2009.
20090323_D120_Redacted_D118, 2009.
20090403_D129_Order_Denying_Motion_to_Dismiss, 2009.
20090408_D130_Redacted_D125_WatsonDefsReplyBrief_iso_MTD_re_AmendedComplaint, 2009.
20090408_D131_Redacted_D126_Park_Decl_iso_Watson_ReplyisoMTD_re_AmendedComplaint, 2009.
20090518_D144_CephalonAnswertoCounterclaims, 2009.
20100212_D187_JointClaim_Construction_Statement, 2010.
20100312_D200_Redacted_D194WatsonOpeningCCBrief, 2010.
20100305_D201_Redacted_D195_Fineman_Decliso_Watson_Opening_CC_Brief, 2010.
20100312_D203_Redacted_D193_PltfsConsolidatedOpeningMarkman, 2010.
20100330_D220_Redacted_D211_WatsonRebuttalMarkmanBrief, 2010.
20100406_D221_Redacted_D210_CephalonRebuttalMarkmanBrief, 2010.
20100408_D230_Redacted_D215_CephalonReplyisoMotiontoModifyPO, 2010.
20100426_D234_Redacted_Pretrial_Order, 2010.
20100503_Public_version_D235_Redacted_Pltfs_Brief, 2010.
20100706_D246_Redacted_D244_Pltfs_Opening_Post_Trial_Brief, 2010.
20100706_D247_Redacted_D245_Dfndnts_Opening_Post_Trial_Brief, 2010.
20100730_D251_PlaintiffsResponsivePost_trial_BriefonValidity, 2010.
20100217 D05 ReportofAction to USPTO, 2010.
20100217 D06 Proof of Service, 2010.
20100217 D06 Sandoz Summons, 2010.
20100310 D07 StiptoExt Time re Answer to Complaint, 2010.
20110928 Mylan Ltr re: Notice of Paragraph IV Certification, 2011.

* cited by examiner

EFFERVESCENT ORAL OPIATE DOSAGE FORMS AND METHODS OF ADMINISTERING OPIATES

CROSS-REFERENCE TO RELATED APPLICATIONS

This application is a continuation of U.S. patent application Ser. No. 11/026,759, filed Dec. 30, 2004 now U.S. Pat. No. 7,862,833, which claims the benefit of U.S. Provisional Patent Application No. 60/533,619, filed Dec. 31, 2003, U.S. Provisional Patent Application No. 60/615,665, filed Oct. 4, 2004, and U.S. Provisional Patent Application No. 60/615,785, filed Oct. 4, 2004, the disclosures of which are hereby incorporated herein by reference.

BACKGROUND OF THE INVENTION

Fentanyl (CAS Registry No. 437-38-7) N-phenyl-N-[1-(2-phenyl-ethyl)-4-piperidinyl] propanamide and its salts, in particular its citrate salt (CAS Registry No. 990-73-8) are opiates, controlled substances, and extremely potent narcotic analgesics. Fentanyl and its citrate salt are currently marketed by a number of companies in a number of delivery formats. Fentanyl citrate, for example, is available as an injectable and an oral lozenge on a stick, the latter sold under the trade name ACTIQ. Three patents are identified in the FDA publication Approved Drug Products With Therapeutic Equivalence Evaluations (hereinafter "the Orange Book") as relating to ACTIQ: U.S. Pat. Nos. 4,671,953, 4,863,737 and 5,785,989.

A review of the package insert information for ACTIQ sold by Cephalon, Inc., 145 Brandy Wine Parkway West, Chester, Pa. 19380, available in the Physician's Desk Reference, 57th ed. 2003 at page 1184, brings instant perspective on the seriousness of the afflictions of the patients who take it. According to its label, ACTIQ "is indicated only for the management of break-through cancer pain in patients with malignancies who are already receiving and who are tolerant to opiate therapy for their underlying persistent cancer pain." (Id., emphasis in original). The text of the ACTIQ label is hereby incorporated by reference. Providing pain relief from such breakthrough pain is inexorably linked with the patient's immediate quality of life. And for such patients, providing breakthrough pain relief may be the only thing that medical science can offer.

Fentanyl is but one of a family of drugs known as opiates. Legal opiates are all prescription drugs and include alfentanil, alphaprodine, anileridine, benzylmorphine, bezitramide, buprenorphine, butorphanol, clonitazene, codeine, codeine phosphate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone, metopon, morphine, morphine hydrochloride, morphine sulfate, myrophine, nalbuphine, narceien, nicomorphine, norlevorphanol, normethadone, normorphine, norpipanone, opium, oxycodone, oxymorphone, papveretum, pentazocine, phenadoxone, phenazocine, phenoperidine, piminodine, piritramide, proheptazine, promedol, propirm, propoxyphene, remifentanil, sufentanil and tilidine. The class of compounds generally known as opiates also includes illicit drugs such as heroin and cocaine. Opiates in accordance with the present invention include those identified above as well as any listed as controlled substances pursuant to 21 C.F.R. §1308.12. Opiates are given to patients for a variety of reasons, most frequently for pain mitigation of one type or another. While the side effects profile is not always the same as that of fentanyl, the class is characterized by very strong drugs, which are both additive and can have lethal side effects, depending upon the dose.

Thus far, fentanyl is unique in opiates in that it has been formulated in an orally disintegrable dosage form. U.S. Pat. No. 6,200,604 ("the '604 patent"), which issued Mar. 13, 2001 to CIMA LABS INC., 10000 Valley View Road, Eden Prairie, Minn. 55344, exemplifies two fentanyl formulations each containing 36% effervescents and 1.57 milligrams of fentanyl citrate. See example I thereof, col. 5, ln. 60 through col. 6, ln. 30. The '604 patent describes the use of, amongst other things, effervescence as a penetration enhancer for influencing oral drug absorption. See also U.S. Pat. Nos. 6,759,059 and 6,680,071. See also Brendenberg, S., 2003 New Concepts in Administration of Drugs in Tablet Form: Formulation and Evaluation of a Sublingual Tablet for Rapid Absorption, and Presentation of an Individualized Dose Administration System, Acta Universitatis Upsaliensis *Comprehensive Summaries of Uppsala Dissertations from the Faculty of Pharmacy*, 287, 83 pp. Uppsala ISBN 91-554-5600-6.

As with many things in medicine, there is always room for improvement. Opiates are expensive drugs. Fentanyl, for example, costs manufacturers as much as $100/gram or more. While cost is by no means an overriding issue, the cost of medication is an issue to be considered. A formulation that allows for a reduction in the amount of opiate could reduce the overall cost of a patient's care.

Far more importantly, a reduction in dose of such a potent opiates while still achieving beneficial management of breakthrough pain in, for example, cancer patients or patients with chronic back pain, has very far reaching and desirable consequences in terms of patients overall care. Opiate mu-receptor agonists, including fentanyl, produce dose dependent respiratory depression. Serious or fatal respiratory depression can occur, even at recommended doses, in vulnerable individuals. As with other potent opiates, fentanyl has been associated with cases of serious and fatal respiratory depression in opiate non-tolerant individuals. And the side effects, even those that are not life threatening, can be significant.

In addition, mu-opiate agonists can produce drug dependence and tolerance. Drug dependence in and of itself is not necessarily a problem with certain types of cancer patients. But, opiates can be used in the treatment of other types of pain as well. In such treatment protocols, dependence and tolerance may be significant issues. Moreover, cancer patients are generally undergoing heavy medication. The longer that a lower dose of medication can be provided, the better.

If lower doses of opiates which nonetheless provide similar pain relief could be achieved, patients could obtain comparable benefit with less drug at lower cost and with a reduced risk of side effects. Thus, improvement in the administration of opiates is still desirable.

SUMMARY OF THE INVENTION

The present invention relates to orally disintegrable/dissolvable effervescent opiate containing dosage forms, methods of using such dosage forms to treat pain and uses thereof for the manufacture of a medicament. In a preferred embodiment, the opiate, or one or more of its pharmaceutically acceptable salts, are administered orally at doses containing less opiate than would be needed in other delivery formations, including the examples in U.S. Pat. No. 6,200,604, to provide a comparable $C_{max}$.

"Oral" dosage form in the context of the invention includes orally disintegrable and/or dissolvable tablets, capsules, caplets, gels, creams, films and the like. Generally, these dosage forms are applied to or placed in a specific place in the oral cavity and they remain there undisturbed while they disintegrate and/or dissolve. The dosage forms of the present invention are preferably designed for buccal, gingival and/or sublingual administration. Dissolution/disintegration, also referred to herein as dwell time, is on average, between about 5 and about 30 minutes, more preferably 10-30 minutes, even more preferably 12-30 minutes. Note that while disintegration and dissolution are distinct concepts, they are used generally interchangeably herein as the time it takes the tablet to cease to exist as an identifiable unit delivery vehicle In another preferred aspect of the present invention, there is provided an orally disintegrable/dissolvable effervescent dosage form, which comprises an effervescent couple, a pH adjusting substance and specific disintigrants, the dosage form being designed for the administration of an opiate and/or pharmaceutically acceptable salts thereof, through the oral cavity such as through buccal, gingival or sublingual administration routes. Without wishing to be bound by a particular theory of operation, it is believed that effervescence acts as a penetration enhancer. The pH adjusting substance is preferably something other than one of the molecules used to generate effervescence and preferably provides a pH difference or change in the microenvironment at the surface contact area if the oral mucosa and the dosage form or any part thereof at of at least about 0.5 pH units when compared to a comparable dosage form without pH adjusting substances. One such embodiment of the invention comprises between about 20 to about 200,000 micrograms of an opiate, between about 0.5 and about 25% by weight of the dosage form ("w/w") of a pH adjusting substance appropriate for said opiate, between about 5 and about 85% w/w of an effervescent couple or material, a starch glycolate and preferably a filler such as mannitol, the dosage form being designed for the administration of the opiate across the oral mucosa through buccal, gingival or sublingual administration routes.

In another particularly preferred embodiment of the present invention, there is provided dosage form consisting essentially of an effective amount of an opiate, calculated as opiate free base, or a proportional amount of a salt thereof, a starch glycolate, at least one pH adjusting substance and at least one effervescent couple. These are all provided in amounts that are effective to form a well-formed, orally disintegrable or dissolvable dosage form and, in an even more preferred embodiment, enable the administration of less opiate to achieve a "comparable" $C_{max}$. Preferably, the mean disintegration time or dwell time will be between 10 and 30 minutes. These mean dwell times are based on multiple dosings of 10 or more patients. These dosage forms are sized, shaped, and designed for buccal, sublingual or gingival administration.

Also contemplated as another aspect of the invention are methods of administering an opiate to patients experiencing pain in general including but not limited to: back pain, lower back pain, joint pain, any form of arthritic pain, pain from trauma or accidents, neuropathic pain, surgical or postoperative pain, pain from a disease or condition other than cancer, cancer pain and in particular, breakthrough pain as a result of cancer. A preferred method includes the steps of administering to a patient in need thereof any orally disintegrable dosage form disclosed herein for buccal, gingival or sublingual administration, which includes an effective amount of an opiate and holding the dosage form in the mouth of the patient for a time sufficient to allow transport of said dose (or a therapeutically significant portion thereof, e.g., enough to reduce a patient's pain) from the oral cavity to the blood stream across the oral mucosa. Preferably, the patient is instructed, trained or watched to ensure that the dose is not swallowed and instead to the extent practicable, the opiate enters the body through one or more of the surfaces within the mouth and oral cavity. The method also preferably includes the step of holding the dosage form in the mouth, substantially without moving it within the oral cavity. In another preferred aspect, the dose dissolves on average in about 30 minutes or less, preferably about 20 minutes or less, and generally 10 minutes or longer. In still another preferred embodiment, the dosage form administered contains less of the same opiate than would normally be given to achieve the intended therapeutic response (intended level of pain relief) based on a dosage form that does not include the effervescent couple, pH adjusting substance and starch glycolate of the invention. In one embodiment, the dosage form achieves comparable $C_{max}$ (80-120%) when compared to an otherwise identical formulation without both said pH adjusting substance and effervescent couple at a dose of opiate which is at least about 20% less w/w.

DETAILED DESCRIPTION

Throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps. "Between" includes the endpoints of a range unless specified elsewhere. "Comparable" in the present invention means that the $C_{max}$ of a dosage form in accordance with the invention will be 80-120% that of an identical dosage form without an effervescent couple, a pH adjusting substance and a starch glycolate.

For purposes of the present invention, unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

A method of administering an opiate to a patient experiencing pain is one aspect of the invention. This method can comprise the steps of contacting the oral mucosa of a patient in need thereof with an orally disintegrable, dosage form. The dosage form includes a single dose of an effective amount of an opiate, generally between about 20 and 200,000 micrograms (measured as a free base), and in another embodiment, between about 50 and about 160,000 micrograms and most preferably between about 50 and about 100,000 micrograms or a proportional amount of a salt thereof. While preferably, the dose is delivered in a single dosage form, it may be spread or divided among two or more dosage forms administered at roughly the same time (e.g., within one hour of each other).

These doses may be repeated up to several times a day as instructed by a treating physician.

In one embodiment, the dosage form is held in contact with the oral mucosa of the patient for a time sufficient to allow transport of a therapeutically significant portion of the opiate, preferably more than 50%, more preferably more than 60% and most preferably 75% or more of the dose, from the oral cavity to the blood stream across the oral mucosa. In another embodiment, the dosage forms of the invention will have an average dwell time in the mouth of between 5 and 30, preferably 10 and 30, more preferably 12 and 30 minutes. This is based on repetitive testing with at least 10 patients.

It has now been discovered that, in certain embodiments, the use of effervescence and a pH adjusting substance, along with specific disintegrants, can provide, in certain embodiments, significant advantages, particularly in terms of the amount of opiate that is required for dosing when compared to similar formulations using different substitutents. It has also been found that certain excipients in combination with effervescent couples and pH adjusting substances can provide very unexpected results. Particularly preferred are effervescent formulations that include a pH adjusting substance and, in addition, starch glycolate. Even more preferred are those that include a mannitol as a filler.

Determining whether or not a particular formulation is capable of achieving the results described herein, one need only undertake a routine human clinical study of that formulation. The appropriate clinical study would use any of the traditional models. Examples of appropriate studies are as follows:

Clinical Study Design and Conduct

This study and Informed Consent Forms (ICF) were Institutional Review Board (IRB) approved. All subjects read and signed an IRB-approved ICF prior to study initiation. Signed and witnessed ICFs are on file.

For the first two periods the study utilized a single-dose, randomized, open-label, 2-way crossover design of the designated test and reference products, and subjects were randomized to receive one of three additional test formulations during Period 3. All subjects were randomized and were in a fasted state following a 10-hour overnight fast. There was a 7-day washout interval between the three dose administrations. The subjects were confined to the clinic through 36 hours post-fentanyl administration.

The subjects were screened within 21 days prior to study enrollment. The screening procedure included medical history, physical examination (height, weight, frame size, vital signs, and ECG), and clinical laboratory tests (hematology, serum chemistry, urinalysis, HIV antibody screen, hepatitis surface antigen screen, hepatitis C antibody screen, serum pregnancy [females only]), and a screen for cannabinoids and opioids.

All subjects enrolled in the study satisfied the inclusion/exclusion criteria as listed in the protocol. A total of 42 subjects, 17 males and 25 females, were enrolled in the study, and 39 subjects, 17 males and 22 females, completed the study.

Subjects reported to the clinic on the morning prior to each dosing and received lunch 19 hours prior to dosing, dinner 14 hours prior to dosing, and a snack 11 hours prior to dosing. The subjects then observed a 10-hour overnight fast. On Day 1, a standardized meal schedule was initiated with lunch at 4.5 hours postdose, dinner at 9.5 hours postdose, and a snack at 13 hours postdose. On Day 2, breakfast was served at 24.5 hours postdose, lunch at 28.5 hours postdose, and dinner at 33 hours postdose.

The subjects were not to consume any alcohol-, broccoli-, citrus-, caffeine-, or xanthine-containing foods or beverages for 48 hours prior to and during each period of confinement. Subjects were to be nicotine- and tobacco-free for at least 6 months prior to enrolling in the study. In addition, over-the-counter medications were prohibited 7 days prior to dosing and during the study. Prescription medications were not allowed 14 days prior to dosing and during the study (excluding hormonal contraceptives for females).

During the study, the subjects were to remain seated for 4 hours after the fentanyl citrate was administered. Water was restricted from Hour 0 until 4 hours postdose. Food was restricted 10 hours predose until 4 hours postdose. During the study, the subjects were not allowed to engage in any strenuous activity.

Subjects received naltrexone at each period as detailed below:

Adm 1: ReVia® 50 mg (naltrexone hydrochloride tablets)
Manufactured by Bristol-Myers Squibb Company
Lot No.: 5C269A
Expiration date: April 2004
Lot No.: TB1798
Expiration date: March 2005

Subjects assigned to Treatments A, B, C, and D received an oral dose of one 50 mg naltrexone tablet taken with 240 mL of water at 15 hours and 3 hours prior to and 12 hours following the fentanyl dose.

Subjects assigned to Treatment E received an oral dose of one 50 mg naltrexone tablet taken with 240 mL of water at 15 hours and 3 hours prior to the fentanyl dose.

Subjects received one of the following fentanyl treatments at each of 3 periods:

A: OraVescent® Fentanyl Citrate Tablets 1080 µg (as fentanyl base)
Manufactured by CIMA LABS INC
Lot No.: 930502

Subjects randomized to Treatment A received a single oral dose of one 1080 µg fentanyl tablet placed between the upper gum and cheek above a molar tooth and allowed to disintegrate for 10 minutes. Note that "OraVescent" indicates a formulation and dosage form in accordance with the present invention.

B: Actiq® (oral transmucosal fentanyl citrate) equivalent to 1600 µg
Manufactured by Cephalon, Inc. or Anesta
Lot No.: 02 689 W3

Subjects randomized to Treatment B received a single oral dose of one 1600 µg Actiq® unit placed between the cheek and lower gum. The unit was to be moved from side to side using the handle and allowed to dissolve for 15 minutes.

C: OraVescent® Fentanyl Citrate Tablets 1300 µg (as fentanyl base)
Manufactured by CIMA LABS INC
Lot No.: 930503

Subjects randomized to Treatment C received a single oral dose of one 1300 µg fentanyl tablet placed between the upper gum and cheek above a molar tooth and allowed to disintegrate for 10 minutes.

D: OraVescent® Fentanyl Citrate Tablets 810 µg (as fentanyl base)
Manufactured by CIMA LABS INC
Lot No.: 930501

Subjects randomized to Treatment D received a single oral dose of one 810 µg fentanyl tablet placed between the upper gum and cheek above a molar tooth and allowed to disintegrate for 10 minutes.

E: OraVescent® Fentanyl Citrate Tablets 270 µg (as fentanyl base)
Manufactured by CIMA LABS INC
Lot No.: 930500

Subjects randomized to Treatment E received a single oral dose of one 270 µg fentanyl tablet placed between the upper gum and cheek above a molar tooth and allowed to disintegrate for 10 minutes.

The composition of each of these fentanyl citrate tablets is described in Examples 1-4.

Sitting vital signs (blood pressure, pulse, and respiration) were assessed each morning prior to dosing (Hour 0) and at 0.25, 0.5, 0.75, 1, 1.25, 1.5, 1.75, 2, 2.25, 2.5, 2.75, 3, 3.25, 3.5, 3.75, 4, 5, 6, 8, 10, 24, and 36 hours postdose. Continuous pulse oximetry was conducted for the first 8 hours postdose. A 12-lead electrocardiogram, a clinical laboratory evaluation (hematology, serum chemistry, and urinalysis), and a physical examination with complete vital signs were performed at the completion of the study. Oral irritation assessments were conducted 4 hours postdose. Subjects were instructed to inform the study physician and/or nurses of any adverse events that occurred during the study.

Blood samples (7 mL) were collected at the following times for subjects assigned to Treatments A-D: predose (Hour 0), and 10, 20, 30, and 45 minutes; and 1, 2, 4, 6, 8, 10, 12, 16, 20, 24, 28, 32, and 36 hours postdose. Blood samples (7 mL) were collected at the following times for subjects assigned to Treatment E: predose (Hour 0), and 10, 20, 30, and 45 minutes; and 1, 2, 4, 6, 8, 9, 10, 11, 12, 14, 16, 20, and 24 hours postdose. A total of 54 blood samples (378 mL) were drawn during the study for drug analysis. Samples were collected and processed at room temperature under fluorescent lighting. Serum samples were allowed to clot, separated by centrifugation, frozen at −20° C., and kept frozen until assayed.

Analytical Methods

An LC-MS/MS (liquid chromatography-mass spectrometry/mass spectrometry) of fentanyl in human serum.

Pharmacokinetic and Statistical Methods

The pharmacokinetic and statistical analysis was based on the Food and Drug Administration, Center for Drug Evaluation and Research (CDER), Guidance for Industry issued January 2001 and entitled "Statistical Approaches to Establishing Bioequivalence," and Guidance for Industry issued March 2003 and entitled "Bioavailability and Bioequivalence Studies for Orally Administered Drug Products—General Considerations."

The following noncompartmental pharmacokinetic parameters were computed from the fentanyl concentration-time data for each treatment using. WinNonlin Standard Edition version 2.1. Actual (rather than nominal) sampling times were used in the analysis.

| | |
|---|---|
| AUC (0-t) | Area under the fentanyl concentration-time curve calculated using linear trapezoidal summation from time zero to time t, where t is the time of the last measurable concentration (Ct). |
| AUC (0-inf) | Area under the fentanyl concentration-time curve from time zero to infinity, AUC (0-inf) = AUC (0-t) + Ct/Kel, where Kel is the terminal elimination rate constant. |
| AUC (0-t)/AUC (0-inf) | Ratio of AUC (0-t) to AUC (0-inf). Also referred to as AUCR. |
| AUC (0-tmax) | The partial area from time 0 to the median Tmax of the reference formulation, calculated using linear trapezoidal summation. |
| Kel | Terminal elimination rate constant calculated by linear regression of the terminal linear portion of the log concentration vs. time curve, where Kel = −slope. The terminal linear portion was determined by visual inspection. |
| T1/2 | Elimination half-life calculated as ln (2)/Kel. |
| $C_{max}$ | Maximum observed fentanyl concentration. |
| $T_{max}$ | Time of the maximum fentanyl concentration (obtained without interpolation). |

This study was a single-dose, randomized, open-label, 2-way crossover of the designated test and reference products. (Treatment A and Treatment B, Periods 1 and 2) with subjects randomized to receive one of three additional test formulations (Treatment C, Treatment D, or Treatment E) during Period 3. Due to the larger number of subjects, the study was run in two groups. The primary comparison in this study was Treatment A versus Treatment B. For the analysis of variance comparing these two treatments, only two sequences (AB, BA), two periods (1, 2), and two treatments (A, B) were considered.

A parametric (normal-theory) general linear model was applied to the log-transformed AUC(0-inf), AUC(0-t), and Cmax values from Treatments A and B.[5-7] The full analysis of variance (ANOVA) model considered group in the model and included the following factors: group, period within group, treatment, sequence, sequence by group, subject within sequence by group, and treatment by group. Since the treatment by group interaction was not significant, the model was reduced to sequence, subject within sequence, period, and treatment. The sequence effect was tested using the subject within sequence mean square and all other main effects were tested using the residual error (error mean square). The two one-sided hypotheses were tested at the 5% level for AUC(0-t), AUC(0-inf), and Cmax by constructing 90% confidence intervals for the ratio of the test and reference means (Treatment A versus Treatment B).

Differences in Tmax for Treatment A and Treatment B were evaluated using the Wilcoxon Signed Ranks Test ($\alpha=0.05$).

Serum fentanyl concentrations and pharmacokinetic parameters were also determined following Treatment C, Treatment D, and Treatment E (1300 µg, 810 µg, and 270 µg OraVescent® Fentanyl Citrate tablet, respectively). In order to evaluate dose proportionality of the OraVescent® Fentanyl Citrate formulation, a mixed linear model was applied to the dose-normalized Cmax and AUC parameters from Treatments A, C, D, and E.[5-7] The full model considered group and included the following terms: group, period within group, treatment, sequence, sequence by group, subject within sequence by group, and treatment by group. The treatment by group interaction was not significant for 2 of the 3 parameters [Cmax and AUC(0-t)] and the model was reduced to a one-way ANOVA with the factor of treatment. If an overall treatment effect was found, pairwise comparisons were performed using Treatment A as the reference.

The dwell time values (length of time the formulation was present in the oral cavity) were calculated by subtracting the treatment administration time from the time of perceived and documented disappearance of the formulation. These values were tabulated and summary statistics were presented.

Results

Demographics and Disposition of Subjects

A total of 42 subjects, 17 males and 25 females, were enrolled in the study, and 39 subjects, 17 males and 22 females, completed the study.

Three subjects were discontinued/withdrawn from the study. One subject was dropped prior to Period 2 because the subject did not want to continue on the study. A second subject was dropped prior to Period 3 because the subject did not want to continue on the study. A third subject was dropped prior to Period 2 because subject took an antibiotic.

The mean age of the subjects was 27 years (range 19-55 years), the mean height of the subjects was 68 inches (range 62-74 inches), and the mean weight of the subjects was 152.1 pounds (range 109.0-197.0 pounds).

Protocol Deviations and Adverse Events

The following protocol deviations occurred during the conduct of the study.

According to the protocol, subjects were to have respirations taken at the 3.5-hour vital signs time point. Respirations were not taken at the 3.5-hour time point for one subject during Period 2. Vital sign recheck was not performed at the 3-hour time point of Period 2 for two subjects. Vital sign recheck was not performed at the 2.25-hour time point of Period 3 for one subject. The blood samples for these two subjects were not labeled properly at the 0.33-hour time point of Period 1 (Treatment A). These samples were not analyzed. According to the protocol, subjects were to have pulse taken at the 3.5-hour vital signs time point. Pulse was not taken at the 3.5-hour time point for one subject during Period 1. No one subject was exposed to more than one of the foregoing deviations. No serious adverse events were reported.

A total of 15 batches were required to process the clinical samples from this study. Of these 15 batches, 14 were acceptable. Back-calculated standard concentrations for the 14 acceptable batches for human serum used in this study covered a range of 50.0 to 5000.0 (pecograms/mL) pg/mL with a limit of quantitation of 50.0 pg/mL. Quality control samples analyzed with each acceptable batch had coefficients of variation less than or equal to 7.89%.

Dwell Time

The dwell time data are summarized in the table below.

| Summary of Tablet/Lozenge Dwell Time | | | | | |
|---|---|---|---|---|---|
| Subject Number | Treatment A Time (Minutes) | Treatment B Time (Minutes) | Treatment C Time (Minutes) | Treatment D Time (Minutes) | Treatment E Time (Minutes) |
| Mean | 21 | 34 | 19 | 25 | 22 |
| SD | 12 | 15 | 11 | 14 | 17 |
| CV | 58 | 44 | 56 | 57 | 75 |
| SEM | 2 | 2 | 3 | 4 | 4 |
| N | 40 | 42 | 12 | 13 | 14 |
| Minimum | 3 | 9 | 4 | 4 | 4 |
| Maximum | 48 | 77 | 33 | 50 | 62 |

Treatment A = 1 × 1080 mcg OraVescent Fentanyl Citrate Tablet: test
Treatment B = 1 × 1600 mcg Oral Transmucosal Fentanyl Citrate (Actiq): reference
Treatment C = 1 × 1300 mcg OraVescent Fentanyl Citrate Tablet: test
Treatment D = 1 × 810 mcg OraVescent Fentanyl Citrate Tablet: test
Treatment E = 1 × 270 mcg OraVescent Fentanyl Citrate Tablet: test
SD = standard deviation; CV = coefficient of variance; SEM = standard error of the mean; N = number (of observations)

One subject reported slight oral irritation (2 on a scale of 1 to 10) that occurred following Treatment C. The irritation was on the right side of the mouth following test product administration during Period 3. There was one report of redness upon visual inspection of the area by study personnel that occurred following Treatment E. The redness was on the right upper cheek following test product administration during Period 3.

Of the 42 subjects enrolled, 40 subjects completed Periods 1 and 2 and were included in the summary statistics, ANOVA analysis, and mean figures for Treatments A and B. Thirty-nine subjects completed Periods 1, 2, and 3 and were included in the statistical analysis for dose proportionality.

The arithmetic means and standard deviations of the serum fentanyl pharmacokinetic parameters and statistical comparisons following Treatment A and Treatment B are summarized in the following table.

| Summary of the Pharmacokinetic Parameters of Serum Fentanyl for Treatments A and B | | | | | | | | |
|---|---|---|---|---|---|---|---|---|
| | Serum Fentanyl | | | | | | | |
| | Treatment A | | | Treatment B | | | | |
| Pharmacokinetic Parameters | N | Arithmetic Mean | SD | N | Arithmetic Mean | SD | 90% CI* | % Mean Ratio |
| Cmax (pg/mL) | 40 | 2704.3 | 877.6 | 40 | 2191.6 | 693.5 | .-. | . |
| AUC(0-tmax) (pg*hr/mL) | 40 | 3840.1 | 1266.2 | 40 | 2566.2 | 911.82 | .-. | . |
| AUC(0-t) (pg*hr/mL) | 40 | 16537 | 5464.6 | 40 | 16701 | 6530.1 | .-. | . |
| AUC(0-inf) (pg*hr/mL) | 35 | 17736 | 5424.3 | 39 | 18319 | 7118.5 | .-. | . |
| T½(hr) | 35 | 11.7 | 5.04 | 39 | 11.2 | 4.37 | .-. | . |
| Kel(1/hr) | 35 | 0.0701 | 0.0310 | 39 | 0.0695 | 0.0227 | .-. | . |
| AUCR | 35 | 0.918 | 0.0458 | 39 | 0.917 | 0.0335 | .-. | . |
| ln(Cmax) | 40 | 7.854 | 0.3132 | 40 | 7.640 | 0.3349 | 111.82-136.20 | 123.4 |
| ln[AUC(0-t)] | 40 | 9.662 | 0.3226 | 40 | 9.649 | 0.3945 | 94.42-108.86 | 101.4 |
| ln[AUC(0-inf)] | 35 | 9.739 | 0.3027 | 39 | 9.742 | 0.3941 | 93.60-109.23 | 101.1 |

Treatment A = 1 × 1080 mcg OraVescent Fentanyl Citrate Tablet: test
Treatment B = 1 × 1600 mcg oral Transmucosal Fentanyl Citrate (Actiq): reference Results of the Wilcoxon Signed Rank Test showed the median Tmax for Treatment A (0.998 hour) was significantly earlier (p<0.0001) compared to Treatment B (1.999 hours).

The individual and mean serum fentanyl pharmacokinetic parameters for Treatments C, D, and E were calculated. There were 5 subjects in Treatment E for whom Kel could not be calculated. Thus, AUC(0-inf), AUCR, and T½ could not be calculated in these cases.

The arithmetic mean and standard deviations of the serum fentanyl pharmacokinetic parameters following Treatments C, D, and E are summarized in the following table.

(Treatment C), 810 µg (Treatment D), or 270 µg (Treatment E). Dose-proportionality of the OraVescent® Fentanyl Citrate tablet formulation (Treatments A, C, D, and E) was evaluated.

A total of 42 healthy subjects were initially enrolled in the study. 39 subjects completed all three periods of the study, and 40 subjects completed both Treatments A and B (Periods 1 and 2). Data from the 40 subjects completing Treatments A and B were included in the pharmacokinetic and statistical analysis.

Summary of the Pharmacokinetic Parameters of Serum Fentanyl for Treatments C, D, and E

| Pharmacokinetic Parameters | Serum Fentanyl | | | | | | | | |
|---|---|---|---|---|---|---|---|---|---|
| | Treatment C | | | Treatment D | | | Treatment E | | |
| | N | Arithmetic Mean | SD | N | Arithmetic Mean | SD | N | Arithmetic Mean | SD |
| Cmax(pg/mL) | 12 | 2791.4 | 874.3 | 13 | 2646.9 | 778.7 | 14 | 797.9 | 312.9 |
| AUC(0-tmax) (pg*hr/mL) | 12 | 4008.3 | 1259.1 | 13 | 3694.8 | 971.89 | 14 | 1095.6 | 433.92 |
| AUC(0-t) (pg*hr/mL) | 12 | 18921 | 6470.2 | 13 | 15339 | 4260.4 | 14 | 4333.5 | 1597.9 |
| AUC(0-inf) (pg*hr/mL) | 12 | 21033 | 7346.3 | 13 | 16831 | 4449.8 | 9 | 4221.9 | 1747.8 |
| T½(Hr) | 12 | 13.2 | 7.67 | 13 | 11.7 | 4.66 | 9 | 6.62 | 3.17 |
| Kel(1/hr) | 12 | 0.0687 | 0.0354 | 13 | 0.0703 | 0.0352 | 9 | 0.126 | 0.0538 |
| AUCR | 12 | 0.907 | 0.0683 | 13 | 0.909 | 0.0376 | 9 | 0.865 | 0.0381 |

Treatment C = 1 × 1300 mcg OraVescent Fentanyl Citrate Tablet
Treatment D = 1 × 810 mcg OraVescent Fentanyl Citrate Tablet
Treatment E = 1 × 270 mcg OraVescent Fentanyl Citrate Tablet
AUCR is ratio of $AUC_{0-t}/AUC_{0-infinity}$ The dose proportionality assessment including p-values for Treatments A, C, D, and E are summarized in the following table.

The ratios of geometric least square means (test/reference) for fentanyl Cmax, AUC(0-t), and AUC(0-inf) were 123.4%, 101.4%, and 101.1%, respectively, for Treatment A versus Summary of the Dose-Normalized Parameters of Serum Fentanyl for Treatments A, C, D and E

| Pharmacokinetic Parameters | P-Value | Serum Fentanyl | | | | | | | | |
|---|---|---|---|---|---|---|---|---|---|---|
| | | Treatment A | | Treatment C | | Treatment D | | Treatment E | | |
| | | Arithmetic Mean | SD | Arithmetic Mean | SD | Arithmetic Mean | SD | Arithmetic Mean | SD | |
| Cmax/dose (pg/mL/mcg) | . | 2.5 | 0.8 | 2.1 | 0.7 | 3.3 | 1.0 | 3.0 | 1.2 | |
| AUC(0-t)/dose (pg*hr/mL/mcg) | . | 15.4743 | 5.01901 | 14.555 | 4.9771 | 18.937 | 5.2597 | 16.050 | 5.9180 | |
| AUC(0-inf)/dose (pg*hr/mL/mcg | . | 16.5851 | 5.00318 | 16.179 | 5.6510 | 20.779 | 5.4935 | 15.637 | 6.4732 | |
| ln(Cmax/dose) | 0.0127 | 0.8788 | 0.3115 | 0.7190 | 0.3151 | 1.137 | 0.3356 | 1.011 | 0.3974 | |
| Ln[AUC(0-t)/dose] | 0.1727 | 2.690 | 0.3170 | 2.625 | 0.3409 | 2.901 | 0.3032 | 2.706 | 0.4002 | |
| ln[AUC(0-inf)/dose] | 0.0783 | 2.765 | 0.3003 | 2.725 | 0.3633 | 2.998 | 0.2894 | 2.691 | 0.3892 | |

Treatment A = 1 × 1080 mcg OraVescent Fentanyl Citrate Tablet
Treatment C = 1 × 1300 mcg OraVescent Fentanyl Citrate Tablet
Treatment D = 1 × 810 mcg OraVescent Fentanyl Citrate Tablet
Treatment E = 1 × 270 mcg OraVescent Fentanyl Citrate Tablet The time intervals over Kel values were determined.

The primary objective of this study was to assess the bioequivalence of a 1080 µg dose of CIMA LABS INC OraVescent® Fentanyl Citrate tablet (Treatment A, test) compared to a marketed 1600 µg oral transmucosal fentanyl citrate, Actiq® (Treatment B, reference) under fasted conditions. The study was a single-dose randomized, open-label, 2-way crossover design for Periods 1 and 2. All subjects also returned in Period 3 for administration of one of three OraVescent® Fentanyl Citrate test formulations: 1300 µg Treatment B. These data indicate that the average fentanyl exposure was similar but the peak exposure was higher for Treatment A compared to Treatment B. The Tmax for Treatment A (0.998 hour) occurred an hour earlier than Treatment B (2.00 hour) and Cmax was 23% higher, indicating that the rate of fentanyl absorption was significantly faster for Treatment A compared to Treatment B.

The 90% confidence intervals for Cmax at 111.82%-136.20%, AUC(0-t) at 94.42%-108.86%, and AUC(0-inf) at 93.60%-109.23% indicated that Treatment A and Treatment B met the requirements for bioequivalence with respect to AUC but not with respect to Cmax. In fact, the Cmax of Treatment A indicates that a dose of about 30-35% less fentanyl by weight given using the OraVescent® formulation exemplified in Example 1 provided a statistically significantly higher Cmax when compared to a 1600 microgram Actiq® formulation. To obtain bioequivalent results in terms of Cmax, indeed to obtain comparable results, one would have to use an OraVescent® fentanyl formulation including at least about 45%, more preferably about 47.5% and even more preferably about 50% less fentanyl (calculated as free fentanyl by weight) than found in the comparator Actiq® tablet. In this instance, approximately 800-880 micrograms was comparable to a 1600 microgram ACTIQ.

Thus it was discovered that, using the present invention and for dosage forms of 1 milligram or less, one could obtain comparable $C_{max}$ with even less fentanyl than initially thought. Rapid $T_{max}$ was also realized. This allowed a further reduction in the doses contemplated with the advantages described previously herein that come from a dose reduction that is not coupled with a reduction in efficacy.

Fentanyl AUC increased proportionally to the dose in the range of 270 to 1300 μg following administration of the OraVescent® Fentanyl Citrate tablet formulation. There were no significant differences in dose-normalized AUC(0-t) or AUC(0-inf) among the 4 OraVescent® doses. A significant overall treatment effect was found for the comparison of dose-normalized Cmax. Pairwise comparisons were performed using Treatment A as the reference because all subjects received Treatment A. No pattern was observed with the pairwise comparisons. A significant difference between Treatment D (810 μg) and Treatment A (1080 μg) was found.

The mean dwell time of the 1080 μg OraVescent® Fentanyl Citrate tablet (21 minutes) was 13 minutes shorter than for Actiq® (34 minutes). Mean dwell times for the other 3 doses of the OraVescent® Fentanyl Citrate tablet formulation (19, 25, and 22 minutes) were similar to 1080 μg OraVescent® formulation.

One subject reported minor irritation to the oral mucosa, and one subject experienced redness following the OraVescent® Fentanyl Citrate tablet. There was no irritation or redness reported following Actiq®.

Comparison of serum fentanyl pharmacokinetics following the administration of 1080 μg OraVescent® Fentanyl Citrate tablet and 1600 μg oral transmucosal fentanyl citrate (Actiq®) showed that the average fentanyl exposure was similar but the rate of absorption was different between the two products. The geometric least squared (LS) mean ratios for AUC(0-t) and AUC(0-inf) were near 100%, and 90% confidence intervals were within 80% to 125%. Geometric LS mean Cmax was 23% higher for 1080 μg OraVescent® Fentanyl Citrate, and the upper limit of the 90% confidence interval for the treatment/reference ratio was greater than 125%, indicating that bioequivalence criteria were not met for this parameter. Thus even further dose reduction could be realized. The Tmax was significantly earlier (1 hour earlier) for the OraVescent® Fentanyl Citrate tablet.

Fentanyl AUC increased proportionally to the dose in the range of 270 to 1300 μg for the OraVescent® Fentanyl Citrate formulation.

The mean dwell time for the 1080 μg OraVescent® Fentanyl Citrate tablet (21 minutes) was 13 minutes shorter than the mean dwell time for Actiq® (34 minutes).

There were no serious or unexpected adverse events during the study. Both formulations were well tolerated by the oral mucosa.

REFERENCES

1. Physician's Desk Reference. 56th ed. Montvale, N.J.: Medical Economics Company, Inc.; 2002. Actiq®; p. 405-409.
2. Fentanyl. Micromedex [online] Vol. 107: Health Series Integrated Index; 2002 [Date Accessed: 2003 Jun. 16]. http://www.tomescps.com
3. Streisand Y B, et al. Dose Proportionality and Pharmacokinetics of Oral Transmucosal Fentanyl Citrate. Anesthesiology 88:305-309, 1998.
4. Naltrexone. Micromedex [online] Vol. 107: Health Series Integrated Index; 2002 [Date Accessed: 2003 Jun. 16]. http://www.tomescps.com
5. SAS Institute, Inc., SAS®/STAT User's guide, Ver. 6. 4th ed. Vol. 1. Cary, N.C.: SAS Institute; 1989.
6. SAS Institute, Inc., SAS®/STAT User's guide, Ver. 6, 4th ed. Vol. 2. Cary, N.C.: SAS Institute; 1989.
7. SAS Institute, Inc., SAS® Procedures guide, Ver. 6, 3rd ed. Cary, N.C.:SAS Institute; 1990.

A second study was performed as well.

This study was conducted to evaluate the extent to which dose proportionality (AUC and Cmax) exists for fentanyl citrate formulated in tablets in accordance with the invention (referred to herein as OraVescent® tablets) over the range that may be used therapeutically, and to confirm the Cmax observations of the study just discussed.

An Institutional Review Board (IRB) approved the protocol and the Informed Consent Form. All subjects read and signed an IRB-approved ICF prior to study initiation. This study had a single-dose, randomized, open-label, 4-treatment, 4-period, crossover design.

The subjects were screened within 21 days prior to study enrollment. The screening procedure included medical history, physical examination (height, weight, frame size, vital signs, and electrocardiogram [ECG]), and clinical laboratory tests (hematology, serum chemistry, urinalysis, HIV antibody screen, hepatitis A antibody screen, hepatitis B surface antigen screen, hepatitis C antibody screen, and serum pregnancy [females only]), and a screen for cannabinoids and opiates.

All subjects enrolled in the study satisfied the inclusion/exclusion criteria as listed in the protocol and the Principal Investigator reviewed medical histories, clinical laboratory evaluations, and performed physical examinations prior to subjects being enrolled in the study. A total of 28 subjects, 16 males and 12 females, were enrolled in the study, and 25 subjects, 14 males and 11 females, completed the study.

Subjects reported to the clinic on the afternoon prior to dosing and received lunch at 1400, dinner at 1900, and a snack at 2200. The subjects then observed a 10-hour overnight fast. On Day 1, a standardized meal schedule was initiated with lunch at 1330, dinner at 1830, and a snack at 2200. On Day 2, a standardized meal schedule (including breakfast) was initiated.

The subjects were not to consume any alcohol, broccoli, caffeine-, or xanthine-containing foods or beverages for 48 hours prior to and during each period of confinement. Grapefruit was restricted 10 days prior to dosing and throughout the study. Subjects were to be nicotine- and tobacco-free for at least 6 months prior to and throughout the completion of the study. In addition, over-the-counter medications (including herbal supplements) were prohibited 7 days prior to dosing and during the study. Prescription medications (including MAO inhibitors) were not allowed 14 days prior to dosing and during the study.

During the study, subjects were to remain in an upright position, sitting, for 4 hours after the fentanyl citrate was administered. Water was restricted from the time of dosing until 4 hours postdose. Food was restricted 10 hours predose until 4 hours postdose. During the study, the subjects were not allowed to engage in any strenuous activity.

Subjects were randomized to receive the following treatments:
Adm1: ReVia® (naltrexone hydrochloride tablets) 50 mg Manufactured by Duramed Pharmaceuticals, Inc.
Lot No.: 402753001T
Expiration date: June 2006.
Subjects received an oral dose of one ReVia® 50 mg tablet taken with 240 mL of water 15 hours and 3 hours prior to dosing for Treatment A.
Subjects received an oral dose of one ReVia® 50 mg tablet taken with 240 ml. of water 15 hours and 3 hours prior to dosing, and 12.17 hours postdose for Treatment B, C, and D.
A: Oravescent® Fentanyl Citrate 200 µg tablets Manufactured by CIMA LABS INC
Lot No.: 930859
Subjects randomized to Treatment A received a single oral dose of one Oravescent® Fentanyl Citrate 200 µg tablet placed between the upper gum and cheek, above a molar tooth, and allowed to disintegrate for 10 minutes.
B: Oravescent® Fentanyl Citrate 500 µg tablets Manufactured by CIMA LABS INC
Lot No.: 930860
Subjects randomized to Treatment B received a single oral dose of one Oravescent® Fentanyl Citrate 500 µg tablet placed between the upper gum and cheek, above a molar tooth, and allowed to disintegrate for 10 minutes.
C: Oravescent® Fentanyl Citrate 810 µg tablets Manufactured by CIMA LABS INC
Lot No.: 930501
Subjects randomized to Treatment C received a single oral dose of one Oravescent® Fentanyl Citrate 810 µg tablet placed between the upper gum and cheek, above a molar tooth, and allowed to disintegrate for 10 minutes.
D: Oravescent® Fentanyl Citrate 1080 µg tablets Manufactured by CIMA LABS INC
Lot No.: 930502
Subjects randomized to Treatment D received a single oral dose of one Oravescent® Fentanyl Citrate 1080 µg tablet placed between the upper gum and cheek, above a molar tooth, and allowed to disintegrate for 10 minutes.

Sitting vital signs (blood pressure, heart rate, and respiratory rate) were assessed each morning prior to dosing and at 0.25, 0.5, 0.75, 1, 1.25, 1.5, 1.75, 2, 2.25, 2.5, 2.75, 3, 3.25, 3.5, 3.75, 4, 5, 6, 8, 10, 24, and 36 hours postdose. Continuous pulse oximetry was obtained for the first 8 hours postdose and whenever the subject attempted to sleep during the first 12 hours postdose. A 12-lead ECG, a clinical laboratory evaluation (hematology, serum chemistry, and urinalysis) and a brief physical examination with complete vital signs were performed at the completion of the study. Oral irritation assessments were conducted 4 hours postdose. At each check-in, the oral cavity was examined to ensure that the subjects did not have canker sores in the area of drug application. Subjects were instructed to inform the study physician or nurses of any adverse events that occurred during the study.

Blood samples (7 mL) were collected at the following times for subjects assigned to Treatment A: Predose (Hour 0), 10, 20, 30, and 45 minutes; and 1, 2, 4, 6, 8, 9, 10, 11, 12, 14, 16, 20, and 24 hours postdose. Blood samples (7 mL) were collected at the following times for subjects assigned to Treatments B, C and D: Predose (Hour 0), 10, 20, 30, and 45 minutes; and 1, 2, 4, 6, 8, 10, 12, 16, 20, 24, 28, 32, and 36 hours postdose.

Human serum samples were analyzed for fentanyl concentrations by a sensitive and specific LC-MS/MS procedure.

The following noncompartmental pharmacokinetic parameters were computed from the fentanyl concentration-time data for each treatment using WinNonlin Standard Edition version 2.1. Actual (rather than nominal) sampling times were used in the analysis.

| | |
|---|---|
| AUC (0-t) | Area under the fentanyl concentration-time curve calculated using linear trapezoidal summation from time zero to time t, where t is the time of the last measurable concentration (Ct). |
| AUC (0-inf) | Area under the fentanyl concentration-time curve from time zero to infinity, AUC (0-inf) = AUC (0-t) ± Ct/Kel, where Kel is the terminal elimination rate constant. |
| AUC (0-t)/AUC (0-inf) | Ratio of AUC (0-t) to AUC (0-inf). Also referred to as AUCR. Kel Terminal elimination rate constant calculated by linear regression of the terminal linear portion of the (log concentration vs. time curve, where Kel = −slope. The terminal linear portion was determined by visual inspection. |
| T1/2 | Elimination half-life calculated as ln (2)/Kel. |
| Cmax | Maximum observed fentanyl concentration. |
| Tmax | Time of the maximum fentanyl concentration (obtained without interpolation). |

Plasma concentration values for fentanyl were listed and summarized by treatment and time point with descriptive statistics (mean, standard deviation [SD], coefficient of variation [CV], standard error of the mean [SEM], sample size, minimum, maximum, and median).[9-11] Values below the lower limit of quantification (LOQ) were set to zero. Mean and individual concentration-time plots were presented. Fentanyl pharmacokinetic parameters and dose-normalized pharmacokinetic parameters were tabulated by treatment and summary statistics were calculated.

Dose proportionality from 200 µg to 1080 µg was assessed using the methodology described by Smith et al.[8] First, log-transformed parameters were analyzed using a mixed effects model including the log-transformation of dose as well as fixed and random effects for intercept. This model was fit using SAS Proc Mixed.[9-11]

A 90% confidence interval (CI) about the fixed effect for slope ($\beta_1$) was calculated and compared to the range (0.8677, 1.1323), which is the appropriate critical range given the range of doses investigated in this study.

Conclusions were based on the following:
1) If the 90% CI for $\beta_1$ was entirely contained within the range (0.8677, 1.1323), dose proportionality was to be concluded.
2) If the 90% CI for $\beta_1$ was completely outside this range, lack of dose proportionality was to be concluded.
3) If the 90% CI for $\beta_1$ was partially in and partially outside this range, the results would be considered "inconclusive." In this case, the value of $\beta_1$ as the best estimate of deviation from ideal proportionality, and the lower and upper bounds of the 90% CI may be considered in the context of drug safety, efficacy, or pharmacological effect data.[8]

In the event that inconclusive results were observed, the maximal dose ratio such that the 90% CI for $\beta_1$ lay entirely within the critical range and the dose ratio such that the 90% CI for $\beta_1$ fell entirely outside the critical range were calculated. These dose ratios are referred to by Smith et al., as ρ1 and ρ2, respectively.

$\rho_1 = \theta_H[1/\max(1-L, U-1)]$, where $\theta_H = 1.25$,
L=the lower limit of the 90% CI,
U=the upper limit of the 90% CI.
$\rho_2 = \theta_H[1/\max(L-1, 1-U)]$, with $\theta_H$, L, and U and defined as above.

A secondary analysis to examine the difference in dose-normalized Cmax between the 3 lowest dose levels (200 μg, 500 μg, and 810 μg) was performed. A parametric (normal-theory) GLM was applied to the dose-normalized Cmax values from Treatments A, B, and C following log-transformation. The analysis of variance (ANOVA) model included the following factors: treatment, sequence, subject within sequence and period. A p-value less than 0.05 was considered statistically significant.

The dwell time values (length of time the formulation was present in the oral cavity) were calculated by subtracting the medication administration time from the time of perceived and documented disappearance of the formulation. These values were tabulated and summary statistics were presented.

Three subjects were discontinued/withdrawn from the study. Two were dropped prior to Period 3 because they did not want to continue on the study. One subject was dropped following dosing on Period 2 because of adverse events. The mean age of the subjects was 33 years (range 19-55 years), the mean height of the subjects was 68.6 inches (range 60-76 inches), and the mean weight of the subjects was 160.9 pounds (range 110-215 pounds).

The following protocol deviations occurred during the conduct of the study. A vital sign recheck was not performed at Hour 0.5 of Period 2 for one subject. A vital sign recheck was not performed at Hour 2.5 of Period 3 for one subject. One subject did not have her serum pregnancy test result available prior to the −15-hour naltrexone dosing on Period 3. The result was made available prior to the −3-hour naltrexone dose. The ECG for Hour 36 of Period 4 was misplaced for one subject. One subject did not have early termination procedures completed. This subject is considered lost to follow-up. And, for all subjects during Period 3, an oral irritation assessment was to have been conducted at 3.83 hours postdose. The nurse responsible for the event recalled performing the assessments but stated that the oral irritation assessment forms were not completed at the time of the event. Therefore, the assessment information cannot be verified and should be considered not done.

The dwell time data are summarized in the table below.

| Subject Number | Treatment A Time (Minutes) | Treatment B Time (Minutes) | Treatment C Time (Minutes) | Treatment D Time (Minutes) |
|---|---|---|---|---|
| MEAN | 14 | 14 | 17 | 15 |
| SD | 8 | 6 | 10 | 11 |
| CV | 59 | 45 | 57 | 72 |
| SEM | 2 | 1 | 2 | 2 |
| N | 25 | 26 | 27 | 27 |
| Minimum | 4 | 6 | 5 | 4 |
| Maximum | 37 | 33 | 41 | 60 |

Treatment A = 200 μg
Treatment B = 500 μg
Treatment C = 810 μg
Treatment D = 1080 μg During the check-in oral cavity assessments it was noted that one subject had a canker sore on the lower right inner cheek at the beginning of Period 4, however, the test product administration during Period 3 occurred on the upper right cheek. The Principal Investigator identified this canker sore as not an apthous ulcer and approved the subject to dose during Period 4.

Two subjects reported slight oral irritation (2 and 3 on a scale of 1 to 10) that occurred following Treatment A. The irritation was on the left side of the mouth following test product administration during Period 2 for both subjects; one of these subjects also exhibited redness upon visual inspection of the area by study personnel. One additional subject reported pain in the upper left buccal area at the gum line 11 minutes following Treatment C. No serious or unexpected adverse events were reported.

Of the 28 subjects enrolled, 25 subjects completed Treatment A, 26 subjects completed Treatment B, and 27 subjects completed Treatments C and D. Statistical analysis was performed on the pharmacokinetic data for all subjects. The elimination rate constant could not be calculated in one subject in Treatment A because there were limited data points in the terminal phase. Thus, AUC(0-inf), AUCR, and T½ could not be calculated for this subject.

The arithmetic means and standard deviations of the serum fentanyl pharmacokinetic parameters following all treatments are summarized in the following table.

Summary of the Phamacokinetic Parameters of Serum Fentanyl
SERUM FENTANYL

| Pharmacokinetic Parameters | Treatment A | | | Treatment B | | |
|---|---|---|---|---|---|---|
| | N | Arithmetic Mean | SD | N | Arithmetic Mean | SD |
| $C_{max}$ (pg/mL) | 25 | 617.8 | 236.7 | 26 | 1546.2 | 621.4 |
| *$T_{max}$ (hr) | 25 | 0.76 | 0.33-4.0 | 26 | 0.75 | 0.33-4.0 |
| AUC(0-t) (pg*hr/mL) | 25 | 2876.3 | 1107.7 | 26 | 8501.2 | 3346.2 |
| AUC(0-inf) (pg*hr/mL) | 24 | 3543.9 | 1304.5 | 26 | 9701.9 | 2651.5 |
| T½(hr) | 24 | 6.48 | 3.69 | 26 | 12.0 | 8.18 |
| Kel(1/hr) | 24 | 0.143 | 0.0802 | 26 | 0.0746 | 0.0377 |
| AUCR | 24 | 0.843 | 0.0604 | 26 | 0.875 | 0.0929 |
| $C_{max}$/dose (pg/mL/mcg) | 25 | 3.09 | 1.18 | 26 | 3.09 | 1.24 |
| AUC(0-t) (pg*hr/mL/mcg) | 25 | 14.4 | 5.54 | 26 | 17.0 | 6.69* |
| AUC(0-inf) (pg*hr/mL/mcg) | 24 | 17.7 | 6.52 | 26 | 19.4 | 7.30 |
| ln($C_{max}$/dose) | 25 | 1.06 | 0.383 | 26 | 1.05 | 0.426 |
| ln[AUC(0-t)/dose] | 25 | 2.59 | 0.424 | 26 | 2.75 | 0.441 |
| ln[AUC(0-inf)/dose] | 24 | 2.81 | 0.369 | 26 | 2.89 | 0.413 |

-continued

Summary of the Pharmacokinetic Parameters of Serum Fentanyl
SERUM FENTANYL

| Pharmacokinetic Parameters | Treatment C | | | Treatment D | | |
|---|---|---|---|---|---|---|
| | N | Arithmetic Mean | SD | N | Arithmetic Mean | SD |
| $C_{max}$ (pg/mL) | 27 | 2280.1 | 968.9 | 27 | 2682.3 | 1106.0 |
| *$T_{max}$ (hr) | 27 | 0.99 | 0.33-4.0 | 27 | 0.75 | 0.33-4.0 |
| AUC(0-t) (pg*hr/mL) | 27 | 13301 | 4069.1 | 27 | 16813 | 5232.2 |
| AUC(0-inf) (pg*hr/mL) | 27 | 14962 | 4709.6 | 27 | 18664 | 6266.0 |
| T½(hr) | 27 | 12.8 | 4.08 | 27 | 11.4 | 4.34 |
| Kel(1/hr) | 27 | 0.0592 | 0.0167 | 27 | 0.0679 | 0.0216 |
| AUCR | 27 | 0.893 | 0.0589 | 27 | 0.909 | 0.0602 |
| $C_{max}$/dose (pg/mL/mcg) | 27 | 2.81 | 1.20 | 27 | 2.48 | 1.02 |
| AUC(0-t) (pg*hr/mL/mcg) | 27 | 16.4 | 5.02 | 27 | 15.6 | 4.84 |
| AUC(0-inf) (pg*hr/mL/mcg) | 27 | 18.5 | 5.81 | 27 | 17.3 | 5.80 |
| ln($C_{max}$/dose) | 27 | 0.945 | 0.439 | 27 | 0.836 | 0.386 |
| ln[AUC(0-t)/dose] | 27 | 2.75 | 0.324 | 27 | 2.69 | 0.356 |
| ln[AUC(0-inf)/dose] | 27 | 2.87 | 0.329 | 27 | 2.79 | 0.372 |

*Median and min-max are reported for Tmax.
Treatment A = 1 × 200 mcg OraVescent Fentanyl Citrate Tablet
Treatment B = 1 × 500 mcg OraVescent Fentanyl Citrate Tablet
Treatment C = 1 × 810 mcg OraVescent Fentanyl Citrate Tablet
Treatment D = 1 × 1080 mcg OraVescent Fentanyl Citrate Tablet The slopes of ln [AUC(0-t)] versus ln(dose) and ln [AUC(0-inf)] versus ln(dose), at 1.0574 and 0.9983, respectively, 1, and the 90% CI for each parameter was completely contained within the critical range required for dose proportionality from 200 μg to 1080 μg. The slope of ln(Cmax) versus ln(dose), 0.8746, was less than 1 and the 90% CI (0.8145-0.9347) was not completely contained within the critical range required for the conclusion of dose proportionality. The maximal dose ratio such that the 90% CI for $\beta_1$ lay entirely within the critical range was 3.33. The maximal dose ratio such that the 90% CI for $\beta_1$ fell entirely outside the critical range was 30.48. The results of the ANOVA of dose-normalized Cmax for Treatments A, B, and C indicate that there was no statistically significant difference in dose-normalized Cmax in the dose range of 200 μg to 810 μg (p=0.13).

The primary objective of this study was to evaluate the extent to which dose proportionality exists for fentanyl AUC and Cmax following fentanyl doses of 200 μg (Treatment A), 500 μg (Treatment B), 810 μg (Treatment C), and 1080 μg (Treatment D) as OraVescent® Fentanyl Citrate tablets. In addition, this study was conducted to confirm previous observations relating to Cmax following the administration of 810 μg and 1080 μg doses of OraVescent® Fentanyl Citrate tablets. This study was a single-dose, randomized, open-label, 4-period crossover design.

Of the 28 subjects enrolled, 25 subjects completed Treatment A, 26 subjects completed Treatment B, and 27 subjects completed Treatments C and D. Statistical analysis was performed on the pharmacokinetic data for all subjects. The slopes of ln [AUC(0-t)] versus ln(dose) and ln [AUC(0-inf)] versus ln(dose), at 1.0574 and 0.9983, respectively, were close to 1, and the 90% CI for each parameter was completely contained within the critical range required for dose proportionality. These results indicate that fentanyl AUC increased proportionally with each increasing dose level of OraVescent® Fentanyl Citrate tablets between the study doses of 200 μg to 1080 μg.

The slope of ln(Cmax) versus ln(dose), 0.8746, was less than 1, indicating that fentanyl Cmax increased less than proportionally to dose. The 90% CI (0.8145-0.9347) was not entirely contained within the critical range. The less than proportional increase was observed at the highest dose (1080 μg) and, to a lesser extent, at the second to highest dose (810 μg). Cmax increased proportionally from 200 μg to 500 μg. The increase in Cmax with dose was "linear" up to and including about 800 μg of fentanyl. The value for $\rho_1$ (maximal dose ratio such that the 90% CI for $\beta_1$ lay entirely within the critical range) was 3.33, whereas the ratio of 810 μg:200 μg is 4.05. This indicates that the formulation is close to meeting the criteria for proportionality from the range of 200 μg to 810 μg according to this method. A secondary analysis using ANOVA to compare dose-normalized Cmax from the 200 μg, 500 μg, and 810 μg doses indicated no statistically significant difference (p=0.13) between these dose levels. The least square ("LS") means for ln(Cmax/dose) were 1.06 (200 μg), 1.06 (500 μg), and 0.94 (810 μg), showing no difference between the 200 and 500 μg doses and a minimal (10%) difference in the 810 μg dose compared to the lower doses. The lack of significant result from the ANOVA in conjunction with the small magnitude in the difference between the 810 μg dose and the 2 lower doses indicates that there is not a clinically important deviation in dose proportionality (linearity) in Cmax from 200 μg to 810 μg.

The mean dwell time for the 200 μg, 500 μg, 810 μg, and 1080 μg OraVescent® Fentanyl Citrate tablets were similar, at 14 minutes, 14 minutes, 17 minutes, and 15 minutes, respectively.

There were 2 subjects who reported minor irritation to the oral mucosa and 1 subject who experienced redness following the OraVescent® Fentanyl Citrate tablet.

Fentanyl AUC increased proportionally with increasing dose in the range of 200 μg to 1080 μg. Fentanyl Cmax increased less than proportionally to dose at the two highest dose levels. Mean ln(Cmax/dose) for the 810 μg dose was 10 to 11% lower than the 200 μg and 500 μg doses. This is linear as defined herein. Mean ln(Cmax/dose) for the 1080 μg dose was 20 to 21% lower than the 200 μg and 500 μg. There was not a clinically important deviation in dose proportionality in Cmax from 200 μg to 810 μg. The mean dwell time for the 200 μg, 500 μg, 810 μg, and 1080 μg OraVescent® Fentanyl Citrate tablets were similar, at 14 minutes, 14 minutes, 17 minutes, and 15 minutes, respectively.

There were no serious or unexpected adverse events during the study. Both formulations were well tolerated by the oral mucosa.

REFERENCES

8. Smith BP, et al. Confidence Interval Criteria for Assessment of Dose Proportionality. Pharmaceutical Research 17:1278-1283, 2000.
9. SAS Institute, Inc., SAS®/STAT User's guide, Ver. 6. 4th ed. Vol. 1. Cary, N.C.: SAS Institute; 1989.
10. SAS Institute, Inc., SAS®/STAT Users guide, Ver. 6, 4th ed. Vol. 2. Cary, N.C.: SAS Institute; 1989.
11. SAS Institute, Inc., SAS® Procedures guide, Ver. 6, 3rd ed. Cary, N.C.: SAS Institute; 1990.
12. Summary Basis of Approval NDA 20-747 (Actiq®). Approval date Nov. 4, 1998, Clinical Pharmacology and Biopharmaceutics Review pp 6.

Formulations in the '604 patent which included lactose monohydrate in an amount of greater than 20% and/or both microcrystalline cellulose in an amount of at least about 20% and cross-linked PVP in an amount of 5% or more are believed to be unable to provide fentanyl formulations having the desirable properties of the invention despite the presence of a pH adjusting substance and an effervescent couple. That is, a greater dose of the opiate would be required to provide a comparable $C_{max}$. Indeed, a 20% dose reduction, or more, can be achieved by use of the present invention. Fentanyl, for example, formulated in the dosage forms of the present invention will have a higher $C_{max}$ at a given dose when compared to those like those in the '604 patent. Thus, to achieve comparable $C_{max}$ less opiate will be necessary. Other opiates should behave in a similar manner. A dosage form which consists essentially of certain fillers in certain amounts would exclude the foregoing as they were not able to achieve the desired comparable $C_{max}$ at the appropriate dose reduction.

The dosage forms in accordance with the present invention will provide effective amounts of opiates that will vary from opiate to opiate and from indication to indication. For fentanyl, for example, an effective amount is an amount between about 100 and about 2000 µg per dose based on the free base form of fentanyl. For demerol the range can go up to as much as 150 mg per dose. Proportionate amounts of a salt, such as a citrate, may also be used.

For oxycodone, the normal daily dose can range from between about 5 to about 160 milligrams. Daily doses of hydromorphone can range from 4 to 45 mg and morphine ranges from 10 to 120 mg.

Generally, the dose of active, to be delivered in one or more dosage forms in accordance with the invention, (per dose, not necessarily per day) will range from between about 20 to about 200,000 micrograms, preferably between about 50 to about 160,000 micrograms, most preferably between about 50 to about 100,000 micrograms.

As an effervescent agent or effervescent couple, any known combination may be used. These include those described in U.S. Pat. No. 5,178,878 and U.S. Pat. No. 5,503,846, the texts of which are hereby incorporated by reference to the extent they discuss various effervescent couples and constructions of same. Effervescent couples generally are water or saliva activated materials usually kept in an anhydrous state with little or no absorbed moisture or in a stable hydrated form. Typically these couples are made of an acid source and a source of a reactive-base, usually a carbonate or bicarbonate. Both may be any which are safe for human consumption.

The acids generally include food acids, acid anhydrides and acid salts. Food acids include citric acid, tartaric acid, malic acid, fumeric acid, adipic acid, ascorbic acid and succinic acid. Acid anhydrides or salts of these acids may be used. Salts in this context may include any known salt but in particular, sodium, dihydrogen phosphate, disodium dihydrogen phosphate, acid citrate salts and sodium acid sulfate. Bases useful in accordance with the invention typically include sodium bicarbonate, potassium bicarbonate and the like. Sodium carbonate, potassium carbonate, magnesium carbonate and the like may also be used to the extent they are used as part of an effervescent couple. However, they are more preferably used as a pH adjusting substance. Preferably, stoichiometric equivalent amounts of acid and base are used. It is possible, however, that some excess of acid or base be used. However, care should be exercised when so formulating a formulation. An excess could affect absorption.

The amount of effervescent material or couple useful in accordance with the present invention is an effective amount and is determined based on properties other than that which would be necessary to achieve disintegration of the tablet in the mouth. Instead, effervescence is used as a basis for enhancing transmission of the opiate across mucosal membranes via buccal, gingival or sublingual administration in the oral cavity. This can be measured by comparing the blood levels of the opiate from a formulation of the invention as compared to an identical formulation without the effervescent couple. Accordingly, the amount of effervescent couple should range from between about 5 to about 85 percent, more preferably between about 15 to 60 percent, even more preferably between about 30 and 45 percent and most preferably between about 35 to about 40 percent, based on the weight of the total formulation ("w/w"). Of course, the relative proportion of acid base will depend upon the specific ingredients (for example, is the acid monoprotic, dipotic or tripotic) relative molecular weights, etc. However, preferably, a stoichiometric amount of each is provided although, of course, excesses may be acceptable.

Preferably, formulations in accordance with the present invention include a pH adjusting substance. Without wishing to be bound by any particular theory of operation, this ensures that a drug which is susceptible to changes in ionization state can be administered by ensuring the proper conditions for its dissolution as well as transmission across one or more of the membranes or tissues within the oral cavity. If the ideal conditions for transmission are basic, the addition of a sufficient excess of suitably strong acid as part of the manufacture of an effervescent couple or as a pH adjusting substance may not be appropriate. The selection of another pH adjusting substance such as, for example, anhydrous sodium carbonate which operates separate and apart from the effervescent agents, are appropriate and preferred.

pH adjusting substances in accordance with the present invention can be used to provide further permeation enhancement. The selection of the appropriate permeation enhancer will depend on the drug to be administered and in particular to the pH at which it is ionized or unionized. A basic substance is "appropriate" for the delivery of fentanyl. Acids may be appropriate for other opiates. pH adjusting substances in accordance with the present invention can include, without limitation, any substance capable of adjusting the localized pH to promote transport across the membranes in the oral cavity in amounts which will result in pH's generally ranging from between about 3 to 10 and more preferably between about 3 to about 9 in the microenvironment at the surface contact area of the oral mucosa and the dosage form or any portion thereof (Also referred to herein as the "localized pH."). To characterize the dynamic pH changes displayed by the tablets in question, an in vitro pH measurement was used.

The method consists of using 0.5-10 mL of phosphate buffered saline in an appropriately sized test tube or similar vessel. The amount of media is dependent on the tablet size and dosage. For example, when measuring the pH profile for fentanyl tablets, a volume of 1 mL was used for tablets which weighed 100 mg. Immediately upon tablet contact with the media, the pH profile of the solution is monitored as a function of time, using a micro-combination pH electrode. Depending on the molecule in question, the combination of effervescence and pH adjusting substance can provide a localized pH ranging from 3-10, and more preferably, it is selected and provided in an amount capable of providing a change in pH of at least 0.5 pH units.

Preferably, the materials which can be used for pH adjusting substances in accordance with the present invention include carbonates such as sodium, potassium or calcium carbonate or a phosphate such as calcium or sodium phosphate. Most preferred is sodium carbonate. The amount of pH adjusting substance useful in accordance with the present invention can vary with the type of pH adjusting substance used, the amount of any excess acid or base from the effervescent couple, the nature of the remaining ingredients and, of course, the drug which, in this case, is fentanyl.

An effective amount of a pH adjusting substance is an amount which is sufficient to change the pH in the localized microenvironment (localized pH) (raise the pH in the case of fentanyl), when dissolved in the mouth, to a pH at which effervescence can enhance the penetration across mucosal membrane in the orally cavity. The effective amount will be capable of providing a pH of between about 3 and about 10. Any pH adjusting substance capable of providing these conditions is contemplated. Preferably, the pH adjusting substance provides a localized pH of 3-10 and more preferably, it is selected and provided in an amount capable of providing a change in localized pH of at least 0.5 pH units. More preferably, an appropriate pH adjusting substance will change the localized pH at the microenvironment by 1 or more pH units, and more preferably 2 or more pH units.

Most preferably the amount of pH adjusting substance will range from between about 0.5 to about 25 percent, more preferably between about 2 to about 20 percent, even more preferably between about 5 to about 15 percent and most preferably between about 7 to about 12 percent by weight based on the weight of the total formulation. The most preferred pH adjusting substance is a carbonate, bicarbonate and the like.

Any filler or any amount of a filler may be used as long as the resulting dosage forms achieve the results described herein. Most preferred amongst the fillers are sugar and sugar alcohols and these may include non-direct compression and direct compression fillers. Non-direct compression fillers generally, at least when formulated, have flow and/or compression characteristics which make them impractical for use in high speed tableting process without some sort of augmentation or adjustment. For example, a formulation may not flow sufficiently well and therefore, a glidant such as, for example, silicon dioxide may need to be added. Typically, these materials could be granulated or spray dried to improve their properties as well.

Direct compression fillers, by contrast, do not require similar allowances. They generally have compressibility and flowability characteristics which allow them to be used directly. It is noted that, depending upon the method by which formulations are made, non-direct compression fillers may be imparted with the properties of direct compression fillers. The reverse is also true. As a general matter, non-direct compression fillers tend to have a relatively smaller particle size when compared to direct compression fillers. However, certain fillers such as spray dried mannitol have relatively smaller particle sizes and yet are often directly compressible, depending upon how they are further processed. There are also relatively large nondirect compression fillers as well. Mixtures of direct and non-direct compression fillers are also contemplated.

Most preferred in accordance with the present invention is mannitol, and in particular, spray dried mannitol. Generally, the amount of filler may range from about 10 to about 80% w/w and more preferably 25 to 80%. Even more preferably, the amount of filler will range from 35 to about 60% by weight of the dosage form or formulation.

Disintegrants may also be used in accordance with the present invention as long as they can provide the results described herein. These may, also include binders that have disintegrating properties. Most preferred for use as a disintegrant is a starch glycolate such as sodium starch glycolate. One sodium starch glycolate useful in accordance with the present invention is GLYCOLYS® (standard grade) from Roquette of Lestrem, France.

The amount of disintegrant will vary with known factors such as, the size of the dosage form, the nature and amounts of the other ingredients used, and the degree of dose reduction sought, etc. However, in general the amount should range from between about 0.25 to about 20% by weight of the final formulation, more preferably between about 0.5 to about 15%, more preferably 0.5 to about 10% w/w, and even more preferably between about one and about eight percent by weight. This is again based on the weight of the finished formulation (dosage form).

Also generally useful in accordance with the present invention is a tableting or ejection lubricant. The most common known lubricant is magnesium stearate and the use of magnesium stearate is preferred. Generally, the conventional wisdom behind tableting lubricants is that less is more. It is preferred in most circumstances that less than one percent of a tableting lubricant be used. Typically, the amount should be half a percent or less. However, the amount of magnesium stearate used can be greater than 1.0%. Indeed, it is preferably greater than 1.5% and most preferably between about 1.5% and about 3%. Most preferred is the use of about 2% magnesium stearate. Other conventional tableting lubricants such as, for example, stearic acid, calcium stearate and the like may also be used in place of some or all of the magnesium stearate.

Effervescent tablets in accordance with the present invention can be relatively soft or robust. They can, for example, be manufactured in accordance with the methods described in U.S. Pat. No. 5,178,878 and will have a hardness of generally less than 15 Newtons. Unlike the formulations described in the '878 patent, the active ingredient here will not necessarily be coated with a protective material. Indeed, preferentially, the opiate active will not be coated. When tablets as soft and pliable/friable as these are produced, they may be advantageously packaged in a blister package such as found in U.S. Pat. No. 6,155,423. They may also be robust with a hardness of greater than 15 Newtons and a hardness of 2% friability or less, manufactured in accordance with the procedures set forth in U.S. Pat. No. 6,024,981.

In a preferred embodiment, the dosage forms of the invention are provided in a blister package which is child resistant. See for example U.S. Pat. No. 6,155,423 to Katzner et al., issued Dec. 5, 2000 and assigned to CIMA LABS INC., the text of which is hereby incorporated by reference. Most preferably, the package meets the standards set forth in 16 U.S.C. §1700.15 and 0.20 (2003). Packages also preferred include those commonly referred to in the industry as so-called "F1" and "F2" packages. "F1" packages are most preferred.

Tablets in accordance with the present invention may be designed slightly differently for buccal, gingival, or sublingual administration. In each instance, however, the in mouth disintegration time (mean dwell time) achieved by the formulations is preferably less than 30 minutes. These tablets will generally exhibit a mean dwell time of between 5 and 30 minutes, more preferably 10 to 30 minutes, most preferably 12 to 30 minutes.

In accordance with a particularly preferred embodiment of the present invention, there is provided an effervescent orally disintegrable tablet designed for buccal, sublingual or gingival administration of an opiate, or pharmaceutically acceptable salt thereof, comprising or consisting essentially of an opiate (by weight based on the weight of the free base), an effective amount of an effervescent couple and an effective amount of a pH adjusting substance. The formulation will further include one or more excipients. In one preferred embodiment, the excipients include mannitol and sodium starch glycolate. In a particularly preferred embodiment, these formulations do not include amounts of lactose monohydrate or both MCC and PVP XL in amounts which significantly reduce the advantages of the invention.

The formulations in accordance with the present invention can include other conventional excipients in generally known amounts to the extent they do not detract from the advantages realized. These can include without limitation binders, sweeteners, coloring components, flavors, glidants, lubricants, preservatives, disintegrants, and the like.

EXAMPLES

Method of Manufacture

In each case for the examples 1-7 and 9-11, materials were screened prior to use, charged into a V-blender, or can be blended in any other appropriate low shear blender, and blended for an appropriate time. After discharge from the blender, the materials were compressed on a standard rotary tablet press to a target hardness of 13 Newtons and a target weight as described in each example.

Example 1

Form A of the First Study

OraVescent® Fentanyl, 1080 mcg, 5/16" Tablet, Red

| COMPONENT NAME | QUANTITY (mg/tab) |
|---|---|
| Fentanyl Citrate, USP | 1.688 |
| Mannitol, USP* | 95.312 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Red Ferric Oxide, NF | 1.000 |
| TOTAL | 200.000 |

*spray dried (mannogem EZ by SPI Pharma)

Example 2

Form C of the First Study

OraVescent® Fentanyl, 1300 mcg, 5/16" Tablet, Red

| COMPONENT NAME | QUANTITY (mg/tab) |
|---|---|
| Fentanyl Citrate, USP | 2.042 |
| Mannitol, USP* | 94.958 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Red Ferric Oxide, NF | 1.000 |
| TOTAL | 200.000 |

*spray dried

Example 3

Form D of the First Study

OraVescent® Fentanyl, 810 mcg, 5/16" Tablet, Yellow

| COMPONENT NAME | QUANTITY (mg/tab) |
|---|---|
| Fentanyl Citrate, USP | 1.266 |
| Mannitol, USP* | 95.734 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Yellow Ferric Oxide, NF | 1.000 |
| TOTAL | 200.000 |

*spray dried

Example 4

Form E of the First Study

OraVescent® Fentanyl, 270 mcg, 5/16" Tablet, White

| COMPONENT NAME | QUANTITY (mg/tab) |
|---|---|
| Fentanyl Citrate, USP | 0.422 |
| Mannitol, USP* | 97.578 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| TOTAL | 200.000 |

*spray dried

Example 5

OraVescent® Fentanyl, 500 mcg, 5/16" Tablet, Orange

| COMPONENT NAME | QUANTITY (mg/tab) |
|---|---|
| Fentanyl Citrate, USP | 0.786 |
| Mannitol, USP* | 96.214 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.600 |
| Red Ferric Oxide, NF | 0.400 |
| TOTAL | 200.000 |

*spray dried

Example 6

OraVescent® Fentanyl, 200 mcg, 5/16" Tablet, White

| COMPONENT NAME | QUANTITY (mg/tab) |
|---|---|
| Fentanyl Citrate, USP | 0.315 |
| Mannitol, USP* | 97.685 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| TOTAL | 200.000 |

*spray dried

Example 7

OraVescent® Fentanyl, 100 mcg, 1/4" Tablet, White

| COMPONENT NAME | QUANTITY (mg/tab) |
|---|---|
| Fentanyl Citrate, USP | 0.157 |
| Mannitol, USP* | 48.843 |
| Sodium Bicarbonate, USP/EP/JP | 21.000 |
| Citric Acid, USP/EP/JP | 15.000 |
| Sodium Carbonate, NF | 10.000 |
| Sodium Starch Glycolate, NF/EP | 3.000 |
| Magnesium Stearate, NF/EP/JP | 2.000 |
| TOTAL | 100.000 |

*spray dried

Example 8

The materials may be screened prior to use, charged into a V-blender or other appropriate low shear blender, and blended for an appropriate time. After discharge from the blender, the materials may be compressed on a standard rotary tablet press to a target hardness of 13 Newtons and a target weight of 200 mg/tablet.

OraVescent® Fentanyl, 300 mcg, 5/16" Tablet, Light Yellow

| COMPONENT NAME | QUANTITY (mg/tab) |
|---|---|
| Fentanyl Citrate, USP | 0.472 |
| Mannitol, USP* | 97.328 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.200 |
| TOTAL | 200.000 |

*spray dried

Example 9

OraVescent® Fentanyl, 400 mcg, 5/16" Tablet, Pink

| COMPONENT NAME | QUANTITY (mg/tab) |
|---|---|
| Fentanyl Citrate, USP | 0.629 |
| Mannitol, USP* | 97.171 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Red Ferric Oxide, NF | 0.200 |
| TOTAL | 200.000 |

*spray dried

Example 10

OraVescent® Fentanyl, 600 mcg, 5/16" Tablet, Orange

| COMPONENT NAME | QUANTITY (mg/tab) |
|---|---|
| Fentanyl Citrate, USP | 0.943 |
| Mannitol, USP* | 96.057 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.600 |
| Red Ferric Oxide, NF | 0.400 |
| TOTAL | 200.000 |

*spray dried

Example 11

OraVescent® Fentanyl, 800 mcg, 5/16" Tablet, Yellow

| COMPONENT NAME | QUANTITY (mg/tab) |
|---|---|
| Fentanyl Citrate, USP | 1.257 |
| Mannitol, USP* | 95.743 |
| Sodium Bicarbonate, USP/EP/JP | 42.000 |

-continued

| COMPONENT NAME | QUANTITY (mg/tab) |
|---|---|
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 1.000 |
| TOTAL | 200.000 |

*spray dried

Example 12

The materials may be screened prior to use, charged into a V-blender or other appropirate low shear blender, and blended for an appropriate time. After discharge from the blender, the materials may be compressed on a standard rotary tablet press to a target hardness of 13 Newtons and a target weight of 200 mg/tablet.

OraVescent® Oxycodone, 5 mg, 5/16" Tablet, White

| COMPONENT NAME | QUANTITY (mg/tab) |
|---|---|
| Oxycodone hydrochloride, USP | 5.000 |
| Mannitol, USP* | 93.000 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| TOTAL | 200.000 |

*spray dried

Example 13

The materials may be screened prior to use, charged into a V-blender or other appropirate low shear blender, and blended for an appropriate time. After discharge from the blender, the materials may be compressed on a standard rotary tablet press to a target hardness of 13 Newtons and a target weight of 200 mg/tablet.

OraVescent® Hydromorphone, 2 mg, 5/16" Tablet, Light Yellow

| COMPONENT NAME | QUANTITY (mg/tab) |
|---|---|
| Hydromorphone hydrochloride, USP | 2.000 |
| Mannitol, USP* | 95.80 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.200 |
| TOTAL | 200.000 |

*spray dried

Example 14

The following materials are weighed and screened.

| # | Description | Qty./Tablet (% w/w) | Qty./Batch (kg) |
|---|---|---|---|
| 1. | Fentanyl Citrate | 0.6285 | 502.8 g* |
| 2a. | Mannitol EZ | 23.875 | 19.1 |
| 2b. | Mannitol EZ | 24.014 | 19.2 |
| 3. | Sodium Bicarbonate, No. 1 | 21.0000 | 16.8 |
| 4. | Citric Acid, Anhydrous, Fine Granular | 15.0000 | 12.0 |
| 5. | Sodium Carbonate, Anhydrous | 10.0000 | 8.000 |
| 6. | Sodium Starch Glycolate | 3.0000 | 2.400 |
| 7. | Yellow 10 Iron Oxide | 0.5000 | 0.400 |
| 8. | Magnesium Stearate, Non-Bovine | 2.0000 | 1.600 |
| | Total | 100.0000 | 80.0 |

Transfer Mannitol EZ (2a.) and Yellow 10 Iron Oxide to V-blender and blend for 30 minutes. Discharge and mill preblend. Add the total quantity of preblend, fentanyl citrate, sodium bicarbonate, citric acid, sodium carbonate and sodium starch glycolate to V-blender and blend for 30 minutes. Charge Mannitol (2b) into V-blender and blend for 13 minutes. Charge magnesium stearate into V-blender and blend for 5 minutes. Compress tablets from this final blend. These tablets are 1/4" round, flat faced, white with a beveled edge. They are compressed to an average hardness of 13 Newtons on a 36 station Fette tablet press fully tooled.

The invention claimed is:

1. A dosage form comprising:
   about 20 to about 200,000 micrograms of an oxycodone,
   about 15 to about 60% of an effervescent material, wherein said effervescent material comprises an acid source and a source of a reactive base;
   about 0.5 to about 25% w/w of a pH adjusting substance, wherein said pH adjusting substance is different from the acid source and the reactive base in the effervescent material,
   a filler, wherein said filler is mannitol; and
   a starch glycolate,
   wherein said dosage form is configured for the delivery of said oxycodone and salts thereof across the oral mucosa as a consequence of buccal, gingival or sublingual administration.

2. The dosage form of claim 1, wherein said pH adjusting substance provides a localized pH of 3 to 10.

3. The dosage form of claim 2, wherein said pH adjusting substance can change the localized pH by at least 0.5 pH units.

4. The dosage form at claim 3 wherein said pH adjusting substance can change the localized pH by at least 1.0 pH units.

5. The dosage form of claim 1, wherein said pH adjusting substance is a carbonate or bicarbonate.

6. The dosage form of claim 1, wherein said starch glycolate is provided in an amount of about 0.5 to about 15% w/w.

7. The dosage form of claim 1 having a mean dwell time in the mouth of a patient of about 5 to about 30 minutes when administered by buccal, gingival or sublingual routes.

8. The dosage form of claim 1 further comprising a binder, a sweetener, a coloring component, a flavor, a glidant, a lubricant, a preservative, a filler and a disintegrant.

9. The dosage form of claim 1 packed in an F1 or F2 blister package.

10. The dosage form according to claim 1 wherein said pH adjusting substance is present in an amount of about 5% to about 15% w/w.

* * * * *